(12) United States Patent
Braido et al.

(10) Patent No.: US 9,693,861 B2
(45) Date of Patent: Jul. 4, 2017

(54) LEAFLET ATTACHMENT FOR FUNCTION IN VARIOUS SHAPES AND SIZES

(71) Applicant: St. Jude Medical, Cardiology Division, Inc., St. Paul, MN (US)

(72) Inventors: Peter N. Braido, Wyoming, MN (US); Jacob John Daly, Blaine, MN (US); Julia Schraut, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/202,939

(22) Filed: Jul. 6, 2016

(65) Prior Publication Data

US 2016/0310269 A1   Oct. 27, 2016

Related U.S. Application Data

(63) Continuation of application No. 14/824,551, filed on Aug. 12, 2015, now abandoned, which is a continuation of application No. 13/781,201, filed on Feb. 28, 2013, now abandoned.

(60) Provisional application No. 61/666,224, filed on Jun. 29, 2012.

(51) Int. Cl.
*A61F 2/24* (2006.01)
*A61F 2/06* (2013.01)

(52) U.S. Cl.
CPC .......... *A61F 2/2418* (2013.01); *A61F 2/2409* (2013.01); *A61F 2/2412* (2013.01); *A61F 2220/005* (2013.01); *A61F 2220/0075* (2013.01); *A61F 2230/0054* (2013.01); *A61F 2230/0067* (2013.01); *A61F 2230/0069* (2013.01)

(58) Field of Classification Search
CPC .................................................... A61F 2/2418
See application file for complete search history.

(56) References Cited

U.S. PATENT DOCUMENTS

| | | |
|---|---|---|
| 3,657,744 A | 4/1972 | Ersek |
| 4,192,020 A | 3/1980 | Davis et al. |
| 4,275,469 A | 6/1981 | Gabbay |
| 4,340,091 A | 7/1982 | Skelton et al. |
| 4,423,730 A | 1/1984 | Gabbay |
| 4,491,986 A | 1/1985 | Gabbay |
| 4,731,074 A | 3/1988 | Rousseau et al. |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |

(Continued)

FOREIGN PATENT DOCUMENTS

WO   WO 2010098857 A1 * 9/2010 ........... A61F 2/2418

*Primary Examiner* — Jacqueline Woznicki
(74) *Attorney, Agent, or Firm* — Lerner, David, Littenberg, Krumholz & Mentlik, LLP

(57) ABSTRACT

A prosthetic heart valve includes a collapsible and expandable stent and a plurality of commissure features disposed on the stent. A collapsible and expandable valve assembly includes a plurality of leaflets connected to the plurality of commissure features, each commissure feature including a body having a proximal end and a distal end. A plurality of eyelets is arranged in rows and columns on the body for distributing load from the plurality of leaflets.

16 Claims, 17 Drawing Sheets

(56) References Cited

U.S. PATENT DOCUMENTS

| | | |
|---|---|---|
| 5,480,423 A | 1/1996 | Ravenscroft et al. |
| 5,843,167 A | 12/1998 | Dwyer et al. |
| 5,855,601 A | 1/1999 | Bessler et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,077,297 A | 6/2000 | Robinson et al. |
| 6,083,257 A | 7/2000 | Taylor et al. |
| 6,090,140 A | 7/2000 | Gabbay |
| 6,168,614 B1 | 1/2001 | Andersen et al. |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,312,465 B1 | 11/2001 | Griffin et al. |
| 6,358,277 B1 | 3/2002 | Duran |
| 6,368,348 B1 | 4/2002 | Gabbay |
| 6,419,695 B1 | 7/2002 | Gabbay |
| 6,425,916 B1 | 7/2002 | Garrison et al. |
| 6,454,799 B1 | 9/2002 | Schreck |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,726,715 B2 | 4/2004 | Sutherland |
| 6,730,118 B2 | 5/2004 | Spenser et al. |
| 6,733,525 B2 | 5/2004 | Pease et al. |
| 6,767,362 B2 | 7/2004 | Schreck |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,830,585 B1 | 12/2004 | Artof et al. |
| 6,869,444 B2 | 3/2005 | Gabbay |
| 6,875,231 B2 | 4/2005 | Anduiza et al. |
| 6,893,460 B2 | 5/2005 | Spenser et al. |
| 6,908,481 B2 | 6/2005 | Cribier |
| 6,916,338 B2 | 7/2005 | Speziali |
| 7,018,406 B2 | 3/2006 | Seguin et al. |
| 7,025,780 B2 | 4/2006 | Gabbay |
| 7,041,132 B2 | 5/2006 | Quijano et al. |
| 7,044,966 B2 | 5/2006 | Svanidze et al. |
| 7,101,396 B2 | 9/2006 | Artof et al. |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,329,278 B2 | 2/2008 | Seguin et al. |
| 7,331,993 B2 | 2/2008 | White |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,871,436 B2 | 1/2011 | Ryan et al. |
| 7,914,569 B2 | 3/2011 | Nguyen et al. |
| 8,034,099 B2 | 10/2011 | Pellegrini |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 8,444,689 B2 | 5/2013 | Zhang |
| D684,692 S | 6/2013 | Braido |
| 8,454,686 B2 | 6/2013 | Alkhatib |
| 8,784,481 B2 | 7/2014 | Alkhatib et al. |
| 8,808,366 B2 | 8/2014 | Braido et al. |
| D730,521 S | 5/2015 | Braido et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0055495 A1 | 3/2003 | Pease et al. |
| 2003/0055496 A1 | 3/2003 | Cai et al. |
| 2003/0130726 A1 | 7/2003 | Thorpe et al. |
| 2003/0153974 A1 | 8/2003 | Spenser et al. |
| 2003/0153975 A1 | 8/2003 | Byrd et al. |
| 2004/0039436 A1 | 2/2004 | Spenser et al. |
| 2004/0049262 A1 | 3/2004 | Obermiller et al. |
| 2004/0088046 A1 | 5/2004 | Speziali |
| 2004/0093060 A1 | 5/2004 | Seguin et al. |
| 2004/0093075 A1 | 5/2004 | Kuehne |
| 2004/0117009 A1 | 6/2004 | Cali et al. |
| 2004/0186563 A1 | 9/2004 | Lobbi |
| 2004/0186565 A1 | 9/2004 | Schreck |
| 2004/0210304 A1 | 10/2004 | Seguin et al. |
| 2005/0075731 A1 | 4/2005 | Artof et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0177227 A1 | 8/2005 | Heim et al. |
| 2005/0192665 A1 | 9/2005 | Spenser et al. |
| 2005/0197695 A1 | 9/2005 | Stacchino et al. |
| 2005/0209689 A1 | 9/2005 | Speziali |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0149360 A1 | 7/2006 | Schwammenthal et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0190074 A1 | 8/2006 | Hill et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0282436 A1 | 12/2007 | Pinchuk |
| 2007/0288087 A1 | 12/2007 | Fearnot et al. |
| 2008/0021552 A1 | 1/2008 | Gabbay |

(56) References Cited

U.S. PATENT DOCUMENTS

| | | |
|---|---|---|
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228263 A1 | 9/2008 | Ryan |
| 2008/0228264 A1 | 9/2008 | Li et al. |
| 2008/0243245 A1 | 10/2008 | Thambar et al. |
| 2008/0243246 A1 | 10/2008 | Ryan et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0114307 A1 | 5/2010 | Agnew et al. |
| 2010/0131054 A1 | 5/2010 | Tuval et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0082539 A1 | 4/2011 | Suri |
| 2011/0098800 A1 | 4/2011 | Braido et al. |
| 2011/0098802 A1 | 4/2011 | Braido et al. |
| 2011/0224678 A1 | 9/2011 | Gabbay |
| 2012/0053681 A1 | 3/2012 | Alkhatib et al. |
| 2012/0078347 A1 | 3/2012 | Braido et al. |
| 2014/0005775 A1 | 1/2014 | Alkhatib et al. |
| 2014/0296966 A1 | 10/2014 | Braido et al. |
| 2015/0066141 A1 | 3/2015 | Braido et al. |
| 2015/0127098 A1 | 5/2015 | Braido et al. |

\* cited by examiner

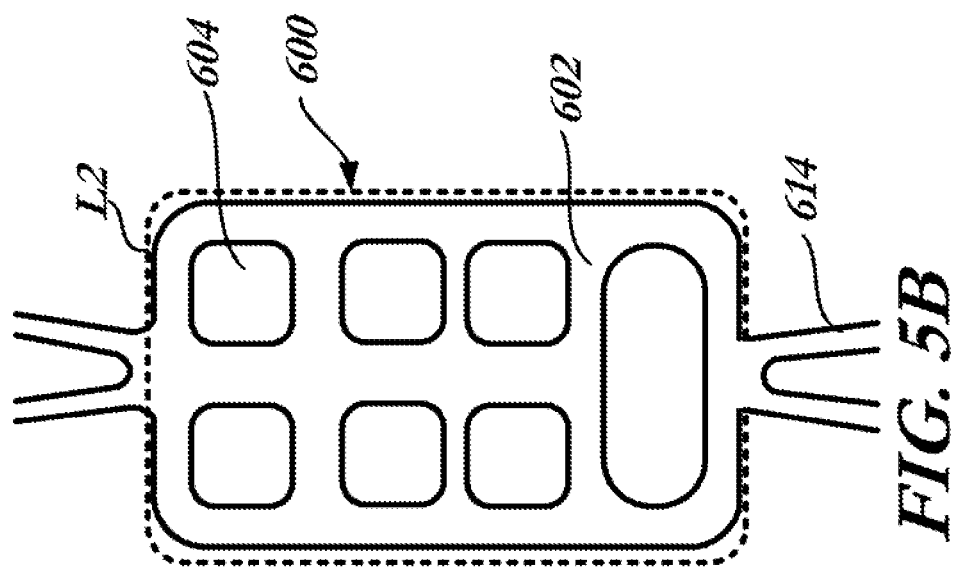
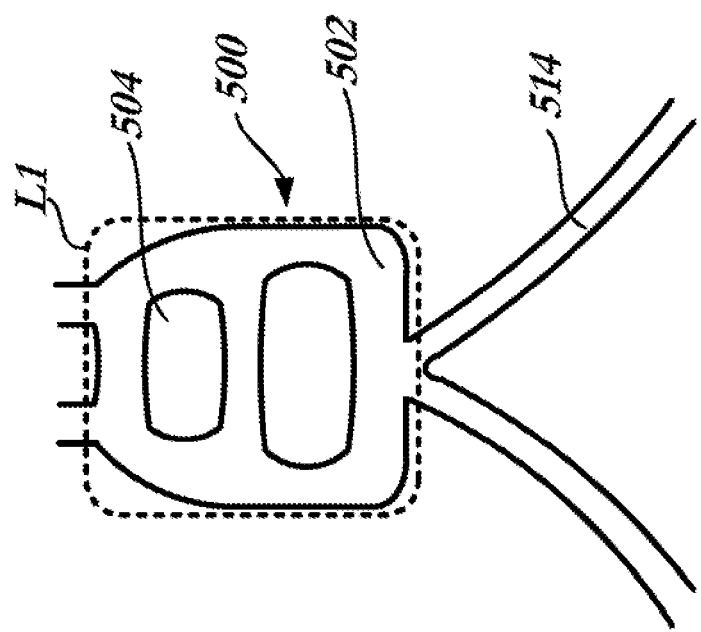

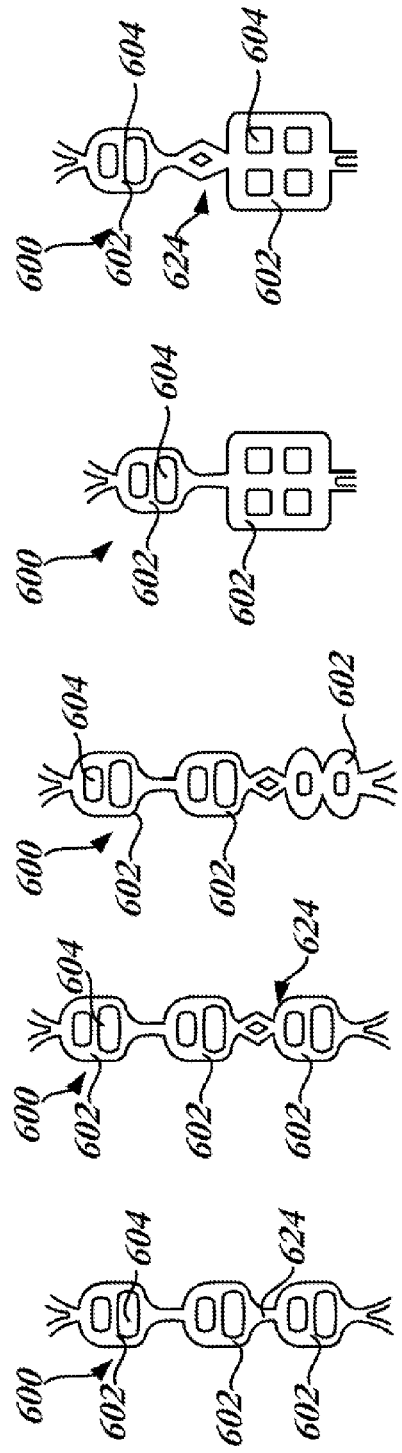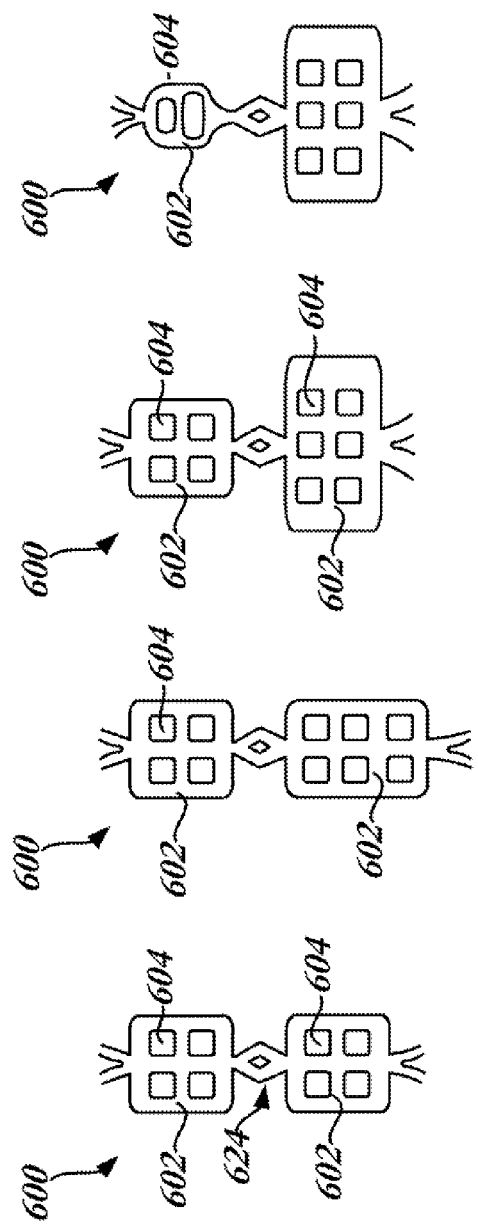

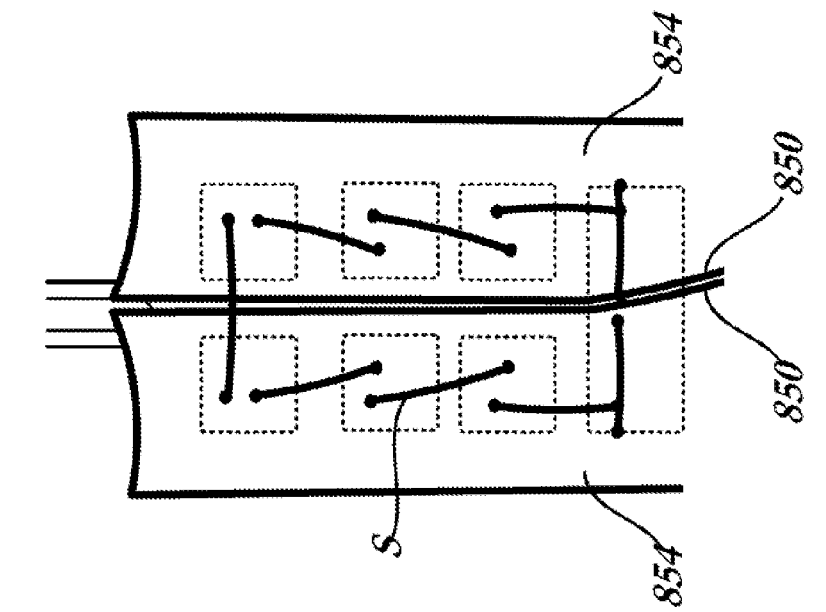
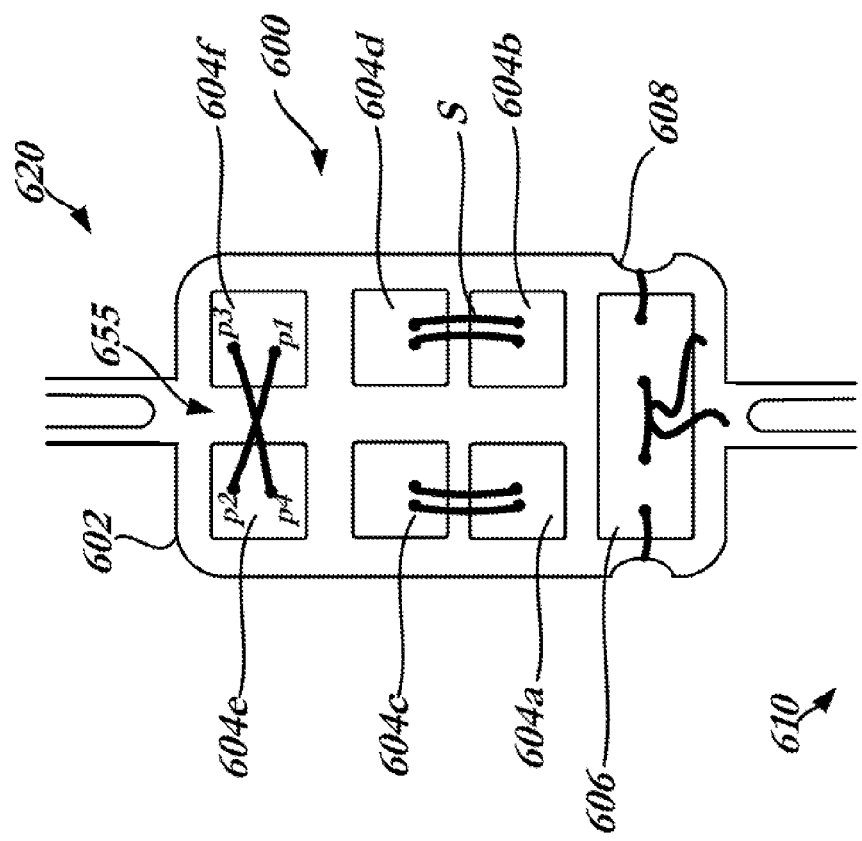
FIG. 11B
FIG. 11A

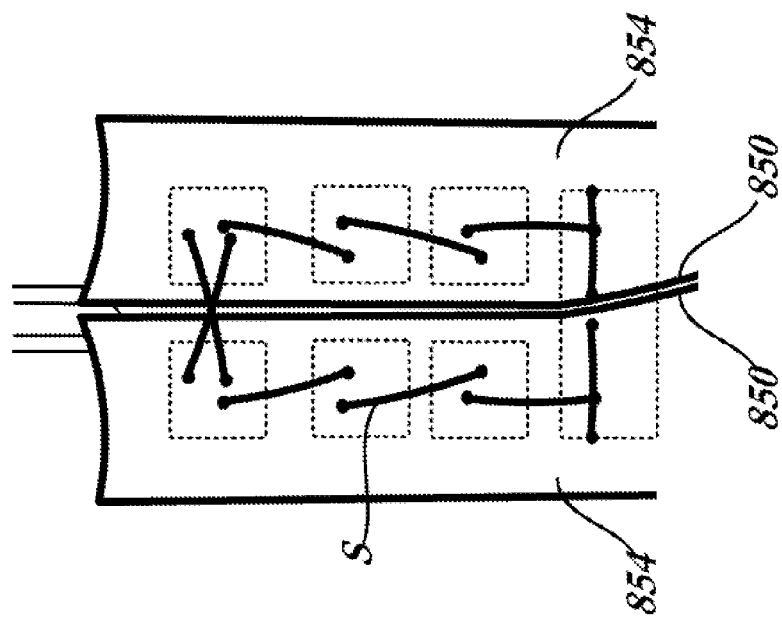
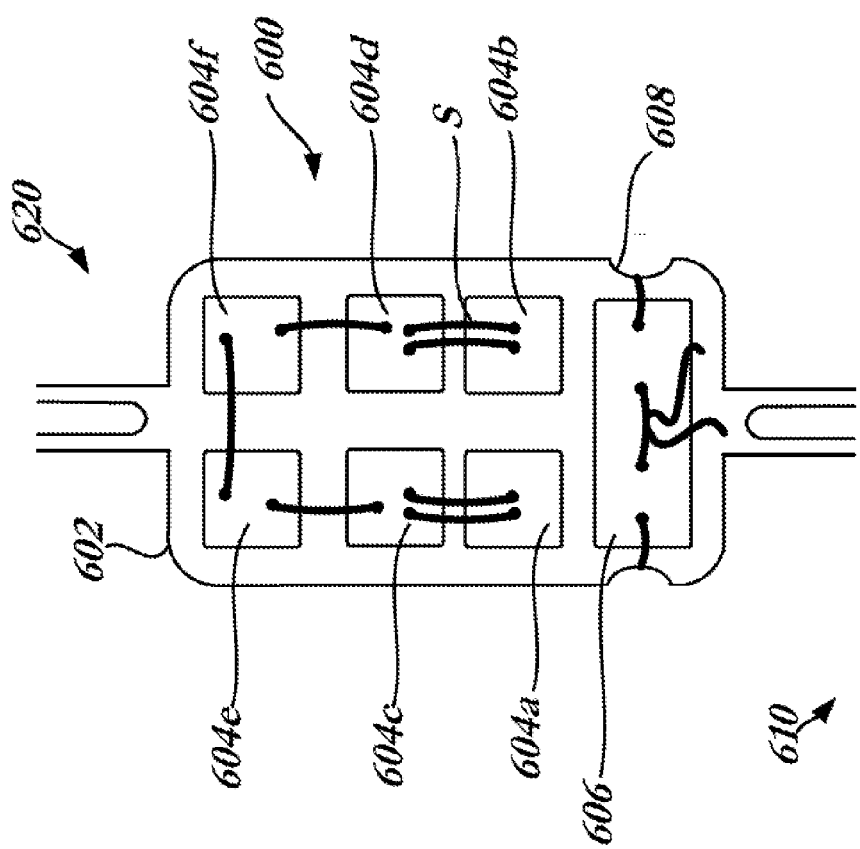
FIG. 12B
FIG. 12A

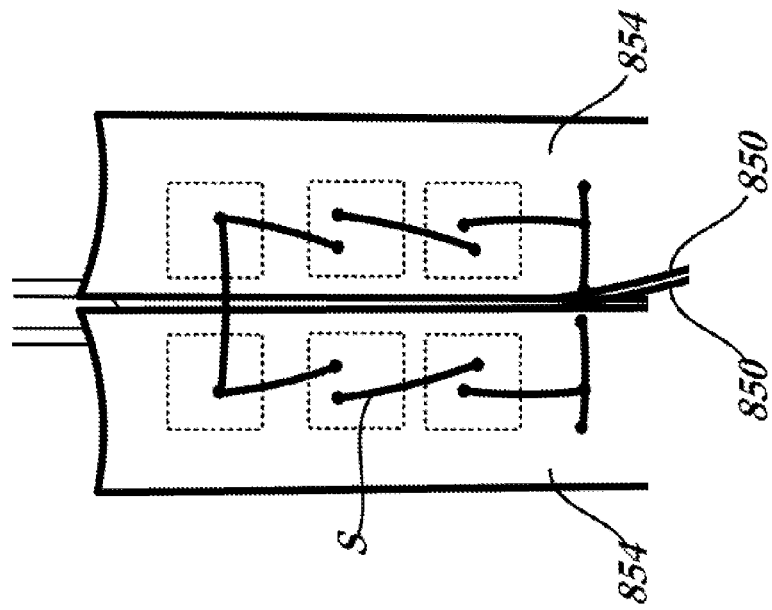
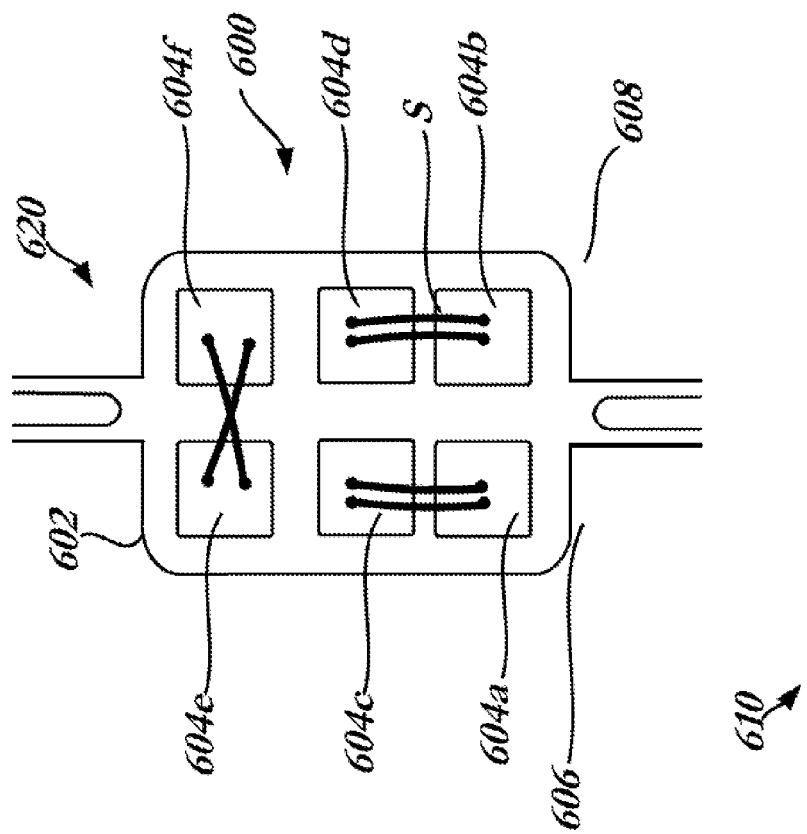

LEAFLET ATTACHMENT FOR FUNCTION IN VARIOUS SHAPES AND SIZES

CROSS-REFERENCE TO RELATED APPLICATIONS

The present application is a continuation of U.S. patent application Ser. No. 14/824,551, filed on Aug. 12, 2015, which is a continuation of U.S. patent application Ser. No. 13/781,201, filed on Feb. 28, 2013, and claims the benefit of the filing date of U.S. Provisional Patent Application No. 61/666,224 filed Jun. 29, 2012, the disclosures of which are all hereby incorporated by reference herein.

BACKGROUND OF THE INVENTION

The present invention relates to heart valve replacement and, in particular, to collapsible prosthetic heart valves. More particularly, the present invention relates to collapsible prosthetic heart valves that may be repositioned during a deployment procedure.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In delivery systems for self-expanding aortic valves, after the delivery system has been positioned for deployment, the annulus end of the valve may be unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheaths the annulus end of the valve, so that the valve can be repositioned while in a collapsed state. After the valve has been repositioned, the user can fully deploy the valve.

Once a self-expanding valve has been fully deployed, it expands to a diameter larger than that of the sheath that previously contained the valve in the collapsed condition, making resheathing impossible, or difficult at best. In order for the user to be able to more readily resheath a valve, it is preferable that the position and operation of the valve be evaluated after the valve has been only partially deployed, with a portion of the valve still collapsed inside of the sheath.

Despite the various improvements that have been made to collapsible prosthetic heart valves, conventional devices, suffer from some shortcomings. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid disease, and/or valve insufficiency could not be treated well, if at all, with the current collapsible designs.

The reliance on evenly calcified leaflets could lead to several problems such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, the optimal valve would seal and anchor adequately without the need for excessive radial force, protrusion into the left ventricular outflow tract (LVOT), etc., that could harm nearby anatomy and physiology.

There therefore is a need for further improvements to the devices and systems of collapsible prosthetic heart valves, and in particular, self-expanding prosthetic heart valves. Among other advantages, the present invention may address one or more of these needs.

SUMMARY OF THE INVENTION

In some embodiments, a prosthetic heart valve includes a collapsible and expandable stent having a proximal end, a distal end, an annulus section adjacent the proximal end and an aortic section adjacent the distal end. The heart valve further includes a plurality of commissure features disposed on the stent and a collapsible and expandable valve assembly, the valve assembly including a plurality of leaflets connected to the plurality of commissure features. Each commissure feature includes a body having a proximal end a distal end, and a plurality of eyelets arranged in at least two rows and at least two columns for distributing load from the plurality of leaflets.

In some examples, each of the plurality of commissure features includes a body that is substantially rectangular. Additionally, each of the plurality of commissure features may include at least three rows of eyelets disposed on the body. Each of the plurality of commissure features may include two columns of eyelets disposed on the body. Each of the plurality of eyelets may be substantially the same shape and/or size.

In some embodiments, a prosthetic valve assembly for assembly to a collapsible and expandable stent includes a stent having a plurality of commissure features, each commissure feature including a body having a longitudinal direction extending between a proximal end and a distal end, and a plurality of eyelets arranged in a plurality of columns each extending in the longitudinal direction, the body having a width in a direction orthogonal to the longitudinal direction. The valve assembly may include a plurality of leaflets, each leaflet having a top free edge for coapting with others of the leaflets and including at least one rectangular tab foldable upon itself along a fold line for attaching to a commissure feature at a leaflet-commissure feature junction, the at least one rectangular tab having a width which is at least as long as the width of the body.

In some examples, the tab includes a distal end extending beyond the distal end of the body when the tab is aligned for attachment to the commissure feature. A flap may be coupled to one side of the tab to provide an additional buffer at the leaflet-commissure feature junction.

In some embodiments a prosthetic heart valve includes a collapsible and expandable stent having a proximal end, a distal end, an annulus section adjacent the proximal end and an aortic section adjacent the distal end. A plurality of commissure features may be disposed on the stent, each commissure feature including a body having a longitudinal direction extending between a proximal end and a distal end, and a plurality of eyelets arranged in at least two columns extending in the longitudinal direction and at least two rows extending in a direction orthogonal to the longitudinal direction, for distributing load from the plurality of leaflets. A collapsible and expandable valve assembly may include a plurality of leaflets connected to the plurality of commissure features via a suture pattern. The plurality of eyelets may be arranged in two columns and the suture pattern forms an "X" pattern between an eyelet in a first of the column and an adjacent eyelet of a second in the columns.

BRIEF DESCRIPTION OF THE DRAWINGS

Various embodiments of the present invention are described herein with reference to the drawings, wherein:

FIG. 5A is an enlarged, schematic side view of a commissure feature of a prosthetic heart valve showing the distribution of load therein;

FIG. 5B is an enlarged, schematic side view of a commissure feature showing the load distribution therein according to one embodiment of the present invention;

FIGS. 11A-B are enlarged, schematic side views showing another suture pattern attaching leaflets to a commissure feature as shown from the ablumenal side and the lumenal side of the valve respectively;

FIGS. 12A-B are enlarged, schematic side views showing a further suture pattern attaching leaflets to a commissure feature as shown from the ablumenal side and the lumenal side of the valve respectively; and FIGS. 13A-B are enlarged, schematic side views showing yet another suture pattern attaching leaflets to a commissure feature as shown from the ablumenal side and the lumenal side of the valve respectively.

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
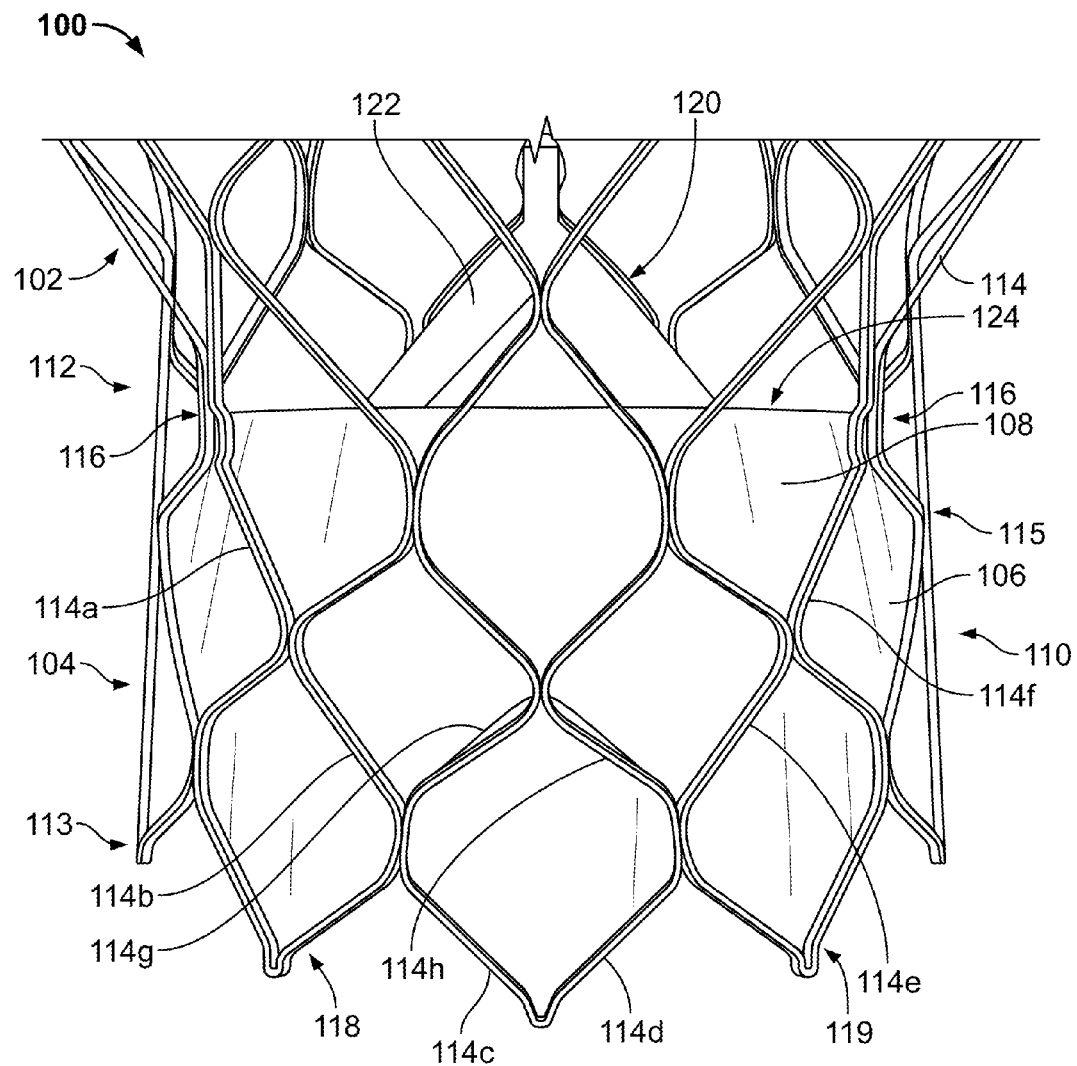
FIG. 1 is a partial side elevational view of a prosthetic heart valve including a valve assembly and a stent.

FIG. 1 shows a collapsible prosthetic heart valve 100 according to an embodiment of the present disclosure. The prosthetic heart valve 100 is designed to replace the function of a native aortic valve of a patient. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyamides. The stent 102 may have an annulus section 110 an aortic section (not shown) and a transition section (not shown) disposed between the annulus section and the aortic section. Each of the annulus section 110, the transition section and the aortic section of the stent 102 includes a plurality of cells 112 connected to one another around the stent. The annulus section 110 and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure features 116 connecting at least two cells 112 in the longitudinal direction of the stent 102. The commissure features 116 may include eyelets for facilitating the suturing of a valve assembly 104 to the sent 102.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester. In at least some examples, portions of valve assembly 104, a cuff and the suture used may include an ultra high molecular weight polyethylene, such as FORCE FIBER®.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. The cuff 106 and/or the sutures used to attach the valve assembly 104 to stent 102 may be formed from or include ultra-high-molecular-weight polyethylene. FIG. 1 shows cuff 106 disposed on the lumenal surface of annulus section 110 so as to cover part of the annulus section while leaving another part thereof uncovered. The cuff 106 may be attached to stent 102 by one or more strings or sutures passing through the cuff and around selected struts 114 of the stent. The valve assembly 104 may further include a plurality of leaflets 108 which collectively function as a one-way valve. A first edge 122 of each leaflet 108 may be attached to the stent 102 between two adjacent commissure features 116 by any suitable attachment means, such as suturing, stapling, adhesives, laser, heat or ultrasonic bonding or the like. For example, the first edge 122 of each leaflet 108 may be sutured to the stent 102 by passing strings or sutures through the cuff 106 of the valve assembly 104. The leaflets 108 may be attached to the stent 102 along at least some struts 114 of the stent and through the eyelets in the commissure features 116 to enhance the structural integrity of the valve assembly 104. A second or free edge 124 of each leaflet 108 may coapt with the corresponding free edges of the other leaflets, thereby enabling the leaflets to function collectively as a one-way valve.

As shown in FIG. 1, at least one leaflet 108 may be attached to the stent 102 so that its first edge 122 is disposed substantially along specific struts 114a, 114b, 114c, 114d, 114e and 114f located in the annulus section 110 of the stent. That is, the edge 122 is positioned in substantial alignment with struts 114a, 114b, 114c, 114d, 114e, and 114f. Struts 114a, 114b, and 114c may be connected to one another in substantially end-to-end fashion diagonally along three cells 112, beginning with an end of the strut 114a connected to a commissure feature 116 and ending with an end of strut 114c connected to an end of strut 114d. Struts 114c and 114d are part of the same cell 112 and may collectively define a substantially right angle between them. Struts 114d, 114e, and 114f may be connected to one another in substantially end-to-end fashion diagonally along three cells 112, beginning with an end of the strut 114f connected to a commissure feature 116 and ending with the connection between an end of strut 114c and an end of strut 114d.

As discussed above, the leaflets 108 may be attached directly to and supported by the struts 114a, 114b, 114c, 114d, 114e, and 114f, and by commissure features 116, such as by suturing. In such event, the cuff 106 may perform little or no supportive function for the leaflets 108. Hence, the cuff 106 is not subjected to high stresses and is therefore less likely to wear during use. In light of this, the thickness of the cuff may be reduced. Reducing the thickness of the cuff 106 results in a decrease in the volume of the valve assembly 104 in the collapsed condition. This decreased volume is desirable as it enables the prosthetic heart valve 100 to be implanted in a patient using a delivery device that is smaller in cross-section than conventional delivery devices. In addition, since the material forming the stent struts 114 is stronger than the material forming the cuff 106, the stent struts 114 may perform the supportive function for the leaflets 108 better than the cuff 106.

The volume of the valve assembly 104 may be further reduced by having the cuff 106 cover only a portion of the surface of annulus section 110. With continued reference to FIG. 1, the first or proximal end 118 of the cuff 106 may substantially follow the contour of the first or proximal end 119 of the stent 102. As such, the proximal end of the cuff 106 may have a generally sinusoidal or zigzag shape. This eliminates any free edge of the cuff 106, which otherwise might extend directly between the cusps of the cells 112 at the proximal end 119 of the stent 102, and enables the entire length of the proximal end 118 of the cuff 106 to be secured to the stent 102. The second or distal end 120 of the cuff 106, on the other hand, may be disposed substantially along at least some struts 114, but not necessarily the struts in a single annular row of cells 112. More particularly, the distal end 120 of the cuff 106 may follow the stent struts 114 up to the commissure features 116, such that the cuff covers all of the cells 112 in the bottom annular row 113 of cells and in a second annular row 115 of cells located between the commissure features and the proximal end 119 of the stent 102, but covers a lesser area of cells in the annular regions between the commissure features. In other words, the distal end 120 of the cuff 106 may be disposed substantially along struts 114a, 114b, 114e, 114f, 114g and 114h, as shown in FIG. 1. Strut 114g may be connected at one end to strut 114h, and at the other end to the intersection of struts 114b and 114c. Strut 114h may be connected at one end to strut 114g, and at the other end to the intersection of struts 114d and 114e. Struts 114c, 114d, 114g, and 114h collectively form a single cell 112.

As a result of the foregoing configuration, all of the cells 112 in the bottom annular row 113 of cells may be entirely covered by the cuff 106. The cuff 106 may also entirely cover those cells 112 in the second annular row 115 that are located directly below the commissure features 116. All of the other cells 112 in the stent 102 may be open or not covered by the cuff 106. Hence, there may be no cells 112 which are only partially covered by the cuff 106.

Since the edges of the valve leaflets 108 extend up to the second annular row 115 of cells 112 only in the regions of the commissure features 116, there is little to no likelihood of leakage in the area of the cells between the commissure features in the second annular row of cells, and therefore no need for the cuff 106 to cover this area. This reduction in the area of the cuff 106, both at the proximal end 118 and at the distal end 120 thereof, reduces the amount of material in the valve assembly 104, thereby enabling the prosthetic valve 100 to achieve a smaller cross-section in the collapsed condition.

In operation, the embodiments of the prosthetic heart valve 100 described above may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device. During delivery, the prosthetic heart valve is disposed inside the delivery device in the collapsed condition. The delivery device may be introduced into a patient using a transfemoral, transapical, transseptal, tranxaxillary or other approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

In certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency could not be treated well, if at all, with the current collapsible designs.

The reliance on evenly calcified leaflets could lead to several problems such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, the optimal valve would seal and anchor adequately without the need for excessive radial force, protrusion into the left ventricular outflow tract (LVOT), etc., that could harm nearby anatomy and physiology.

Figure 2A:
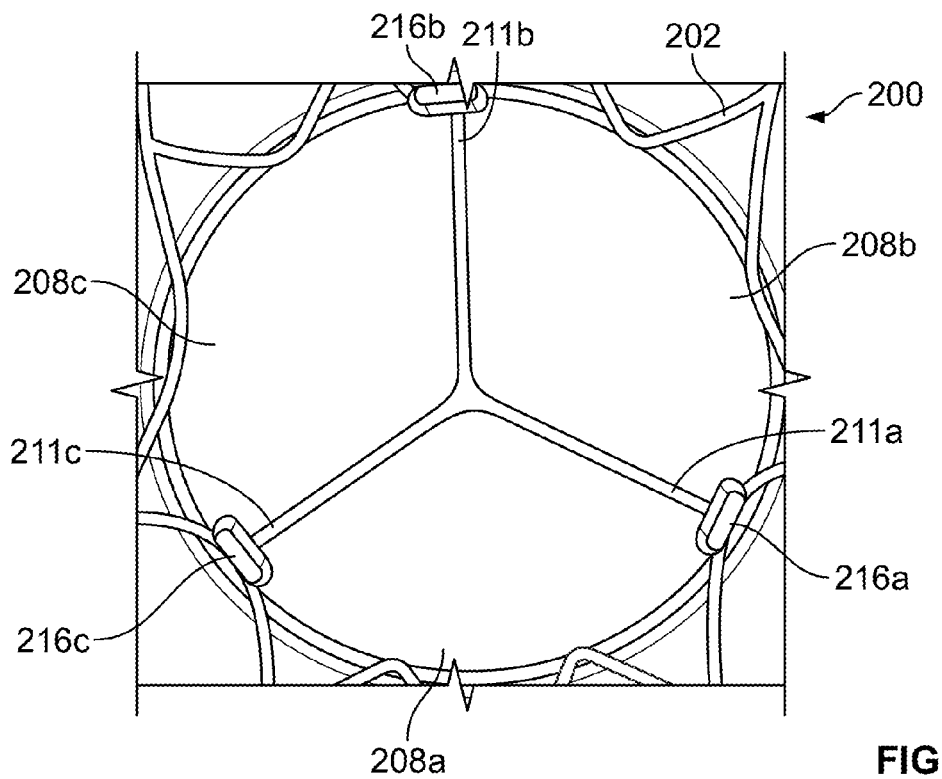
FIG. 2A is an end view of a prosthetic heart valve as seen from the aortic sinus toward the heart and the native valve annulus, the valve having in a circular configuration.
Figure 2B:
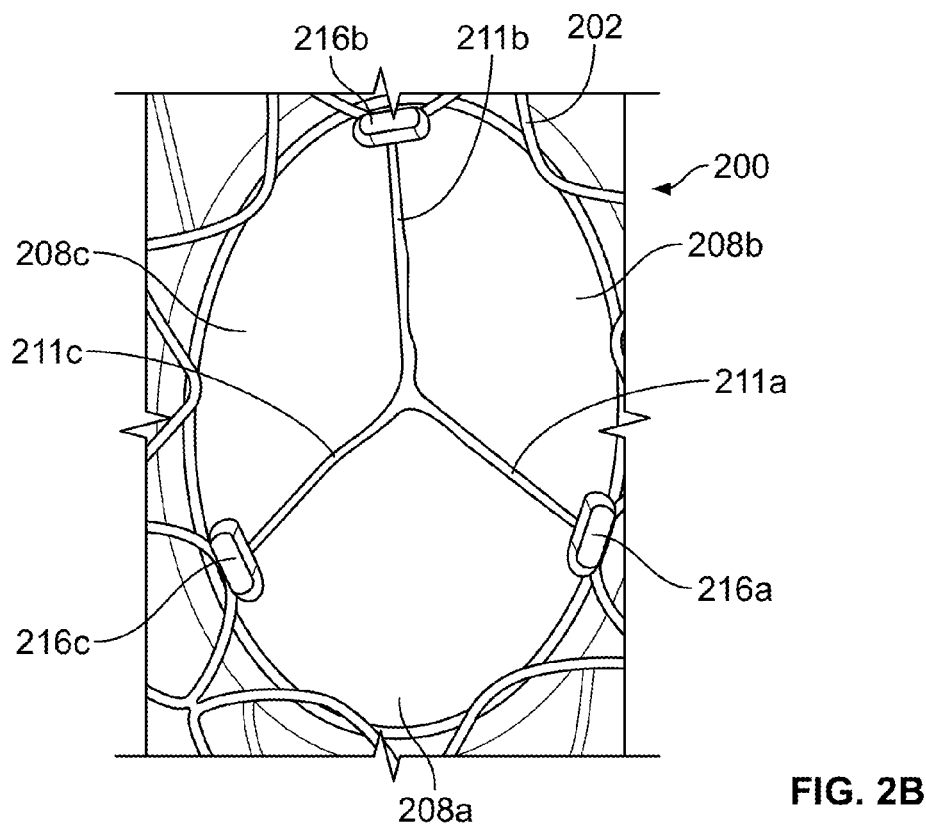
FIG. 2B is an end view of a prosthetic heart valve as seen from the aortic sinus toward the heart and the native valve annulus, the valve having an elliptical configuration.

FIGS. 2A and 2B show an end view of a prosthetic heart valve 200 as seen from the outflow or downstream side of the valve assembly, e.g., looking from the aorta or aortic sinus toward the heart and the native valve annulus. As seen in FIG. 2A, the valve assembly includes a stent 202 and valve leaflets 208a, 208b, and 208c attached to the stent and to commissure features 216a, 216b, and 216c. At least one edge of each leaflet 208 is sutured to the stent 202 and to two of the three commissure features 216, leaving at least one edge free to move in response to the pumping of blood. As the blood pressure in the left ventricle increases, the free edges of the leaflets move away from one another to allow blood to flow from the left ventricle to the aorta, following which the free edges move toward one another and coapt to prevent blood from flowing back from the aorta into the left ventricle.

It will be understood that the coaptation of "the free edges" of the valve leaflets does not necessarily mean that the actual edges meet per se. Indeed, the leaflets are preferably sized, shaped, and attached such that a suitable "belly" contour is formed. And the leaflets should each include a portion extending from the free edge toward the annulus (referred to herein as a "coaptation section") that may engage the coaptation sections of the other leaflets such that there will be a surface area of contact between the leaflets rather than edge-to-edge contact. This surface area of contact is important so that, when in a closed or "coapted" condition, the leaflets cooperate to substantially prevent backflow or regurgitation of blood through the valve. These areas of actual contact between the coaptation sections of adjacent leaflets are referred to herein as the coaptation junctions of the leaflets and are illustrated in FIG. 2A at 211a, 211b, and 211c. The coaptation section of each leaflet may range in size as a particular valve design demands, but generally will be sufficient to provide some tolerance or ability to form a coaptation junction even if the shape of the valve is distorted during placement, as illustrated in FIG. 2B.

The annulus section of prosthetic heart valve 200 has a generally regular cylindrical shape by which is meant that the structure has a generally circular cross-section with a substantially constant diameter along its length. When placed in the annulus of a native heart valve, such as, for example, the tricuspid aortic valve, and expanded, a substantially fluid-tight fit should result. However, the native valve annulus may not be circular, and, in fact, may vary from patient to patient, as may the shape of the aortic sinus or aorta, the angle of the junction between the valve annulus and the aortic sinus, and other local anatomical features. When prosthetic heart valve 200 is deployed and expanded, it must accommodate these anatomical variations in order to function properly. This may result in a distortion in the shape of stent 202 and/or valve assembly 204, and the repositioning of leaflets 208a, 208b, and 208c relative to one another, which can affect the coaptation junctions 211a, 211b, and 211c.

As the stent of a collapsible prosthetic heart valve distorts during implantation, during beating of the heart, or because of irregularities in the patient's anatomy or the condition of the native valve, such distortion may be translated to the valve assembly, such that not all of the valve leaflets meet to form effective coaptation junctions. This can result in leakage or regurgitation and other inefficiencies which can reduce cardiac performance. Moreover, if the prosthetic valve is not placed optimally and the valve leaflets are not coapting as intended, other long term effects, such as uneven wear of the individual leaflets, can be postulated.

As shown in FIG. 2B, ideally, valve leaflets 208a, 208b, and 208c fully coapt despite the distortion of the annulus section (hidden behind the valve leaflets in this figure) into a more elongated or elliptical configuration. As will be appreciated, the distortion of the annulus section affects the relative positions of commissure features 216a-c, as well as the positions of leaflets 208a-c relative to one another. The ability of the valve leaflets 208a-c to fully coapt despite this distortion enables prosthetic valve 200 to function in the manner intended.

Figure 3A:
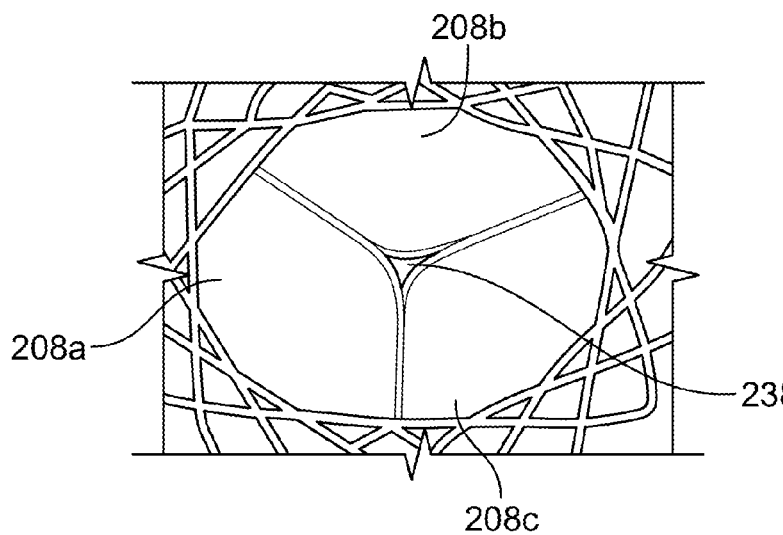
FIGS. 3A-C are end views of the prosthetic heart valve of FIG. 1 in various less than ideal configurations due to anatomical differences in the native valve morphology from patient to patient.
Figure 3B:
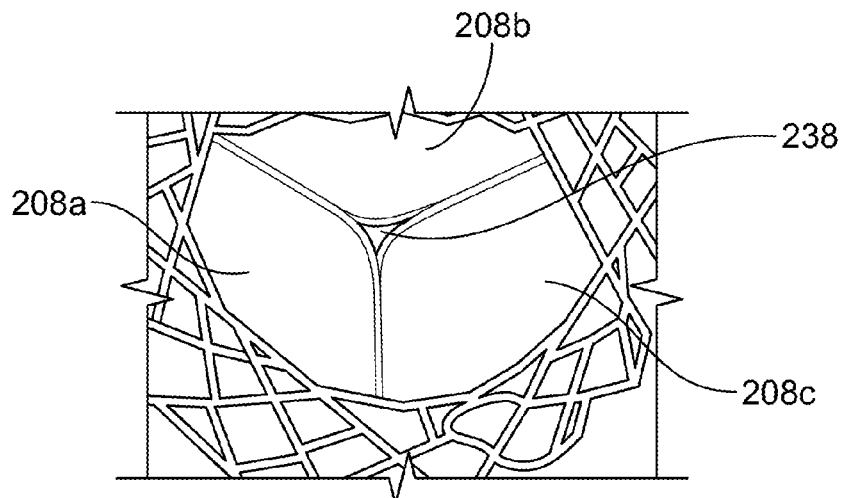
Figure 3C:
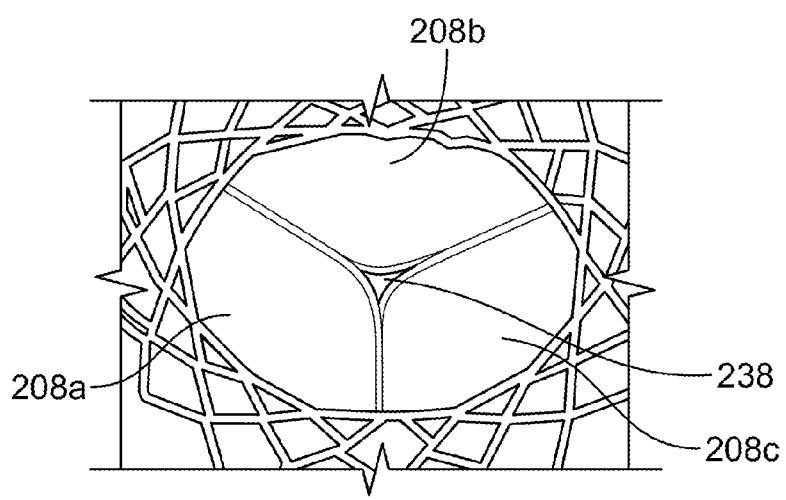

FIGS. 3A-C illustrate a series of prosthetic heart valve as seen from the downstream side of the valve assembly, e.g., looking from the aorta or aortic sinus toward the heart and the native valve annulus. Each of these valves has an elliptical configuration resulting from the shape of the native valve annulus, calcification and possibly other defects. As seen in FIGS. 3A-C, the imperfect geometry the valve assumes results in inadequate coaptation of the leaflets 208a-c. Specifically, the leaflets 208 of these valves are incapable of complete coaptation when disposed in a native valve annulus with an elliptical, ovoid or otherwise non-circular configuration. In some examples, a gap 238 may be evident between the leaflets 208 in what should be the fully closed condition. Such inadequate coaptation may lead to leakage and regurgitation as discussed above.

Figure 4:
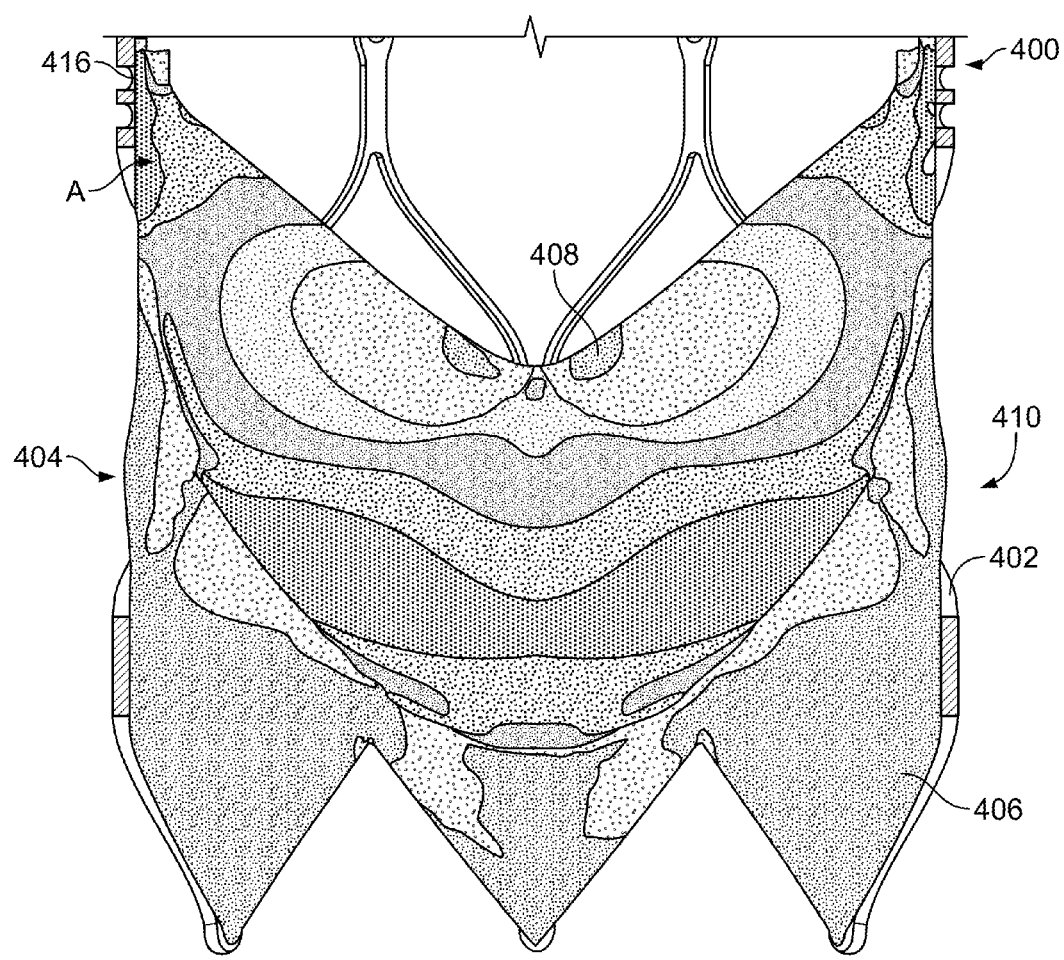
FIG. 4 is a partial side elevational view of the prosthetic heart valve of FIG. 1 depicting areas of high stress on the valve assembly.

In addition to inadequate coaptation, less than ideal native valve geometry may also increase the stresses on certain portions of the prosthetic heart valve. FIG. 4 is a partial side view of a prosthetic heart valve 400 having a stent 402 and a valve assembly 404 disposed in the annulus section 410 of the stent. Within the heart valve 400, leaflets 408 are attached to cuff 406 via sutures. Specifically, FIG. 4 shows the load distribution in the valve assembly. When leaflets 408 coapt to form a closed configuration, load is transferred from the leaflet structure to the leaflet-commissure feature junction as indicated by "A". The load distribution diagram shows that high point loads are generated at region "A" where the leaflets are joined to the commissure feature 416. If the point loads at regions "A" are sufficiently high, the leaflets may tear from the commissure feature. Thus, regions A may be prone to failure.

Features of this aspect of the present invention will be described in connection with the commissure features shown in FIGS. 5A and 5B. It will also be noted that while the inventions herein described are predominately discussed in terms of a tricuspid valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

FIG. 5A illustrates a previous version of a commissure feature 500 coupled to struts 514 for attaching a valve assembly to the stent. Commissure feature 500 is formed of a body 502 having a pair of eyelets 504. Leaflets (not shown) may be attached via sutures to commissure feature 500 through eyelets 504 and struts 514. Load is distributed across the area of commissure feature 500 as shown in FIG. 5A. Specifically, stress from the leaflets is distributed across area L1 of the commissure feature 500.

FIG. 5B illustrates a commissure feature 600 coupled to struts 614 according to one embodiment of the present invention. Commissure feature 600 is formed of a body 602 having a plurality of eyelets 604 arranged in rows and/or columns. Leaflets (not shown) may be attached via sutures, glue, staples or any suitable means to commissure feature 600 through eyelets 604 and struts 614. Stress from the leaflets is distributed across area L2 of the commissure feature 600, as shown in FIG. 5B. Details of commissure feature 600 will be described in greater detail with reference to FIGS. 6A-J. It will suffice to note at this point that a comparison of FIGS. 5A and 5B illustrates the difference in the area for load distribution between commissure features 500 and 600. Specifically, commissure feature 600 provides a larger area L2 across which the stress from the leaflets is distributed when compared to area L1 of commissure features 500. A larger area for distributing loads may decrease the chance of failure at the commissure feature-leaflet attachment. Moreover, increasing the spacing between eyelets 604 may allow the valve to function better acutely and chronically. The benefit of wider-spaced eyelets may be recognized in improved ease of manufacturing, which in turn generally leads to improved yields for functional and visual valve criteria. Ease of manufacturing reduces the likelihood for tolerance stack-ups related to tissue folding and alignment. This may also reduce need for pinching or manipulation of the valve during assembly.

FIGS. 6A-J illustrates several specific embodiments of commissure features according to the present invention, all of which have the same general shape and characteristics. It will be appreciated that the commissure features described in these figures are exemplary and should not be considered limiting. Moreover, the described features in the following embodiments may be combined or modified in any desirable manner.

Figure 6A:
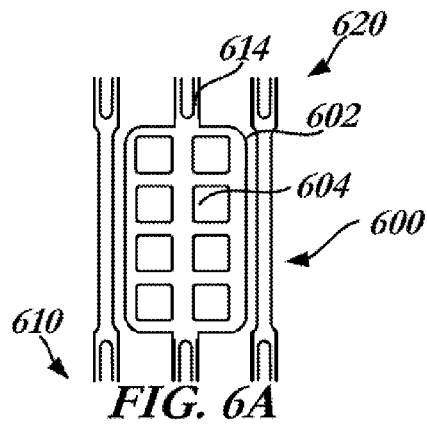
FIGS. 6A-S are enlarged schematic side views of several embodiments of commissure features according to the present invention.

FIG. 6A illustrates a commissure feature 600 according to one embodiment of the present invention. Commissure feature 600 includes a body 602 having a proximal end 610 and a distal end 620, and a plurality of eyelets 604 disposed therein. Specifically, the commissure feature 600 of FIG. 6A includes four rows of eyelets 604 along the length of body 602, each row including two eyelets so as to form two columns of eyelets. The rows of eyelets 604 may be evenly spaced and of the same shape and size, as illustrated in FIG. 6A, so as to be symmetrical with respect to a central longitudinal axis of body 602. As depicted, the eyelets 604 are all in the shape of similarly sized squares. Body 602 is coupled to struts 614 at its proximal end 610 and distal end 620. Leaflets (not shown) may be attached via sutures to commissure feature 600 through eyelets 604.

Figure 6B:
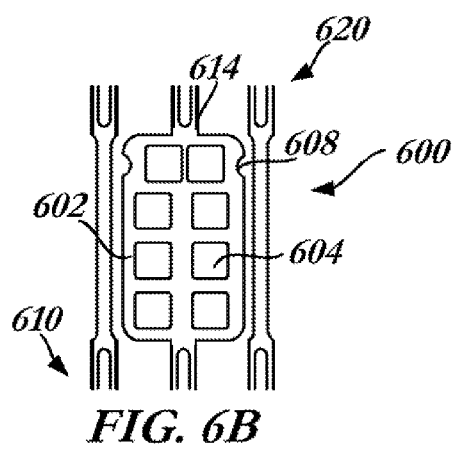

FIG. 6B illustrates a second embodiment of commissure feature 600 which is similar to that of FIG. 6A, with two exceptions. First, recesses 608 are disposed on the side edges of the body 602 near the distal end 620. Recesses 608 may be formed as indentations or depressions in body 602 and sutures may be wrapped around or disposed within the recesses. Such recesses may be useful in not only securing and guiding a suture, but also in protecting the suture from adjacent cells, a delivery system or other anatomical bodies that may damage it. Second, the plurality of eyelets 604 are not evenly spaced in FIG. 6B. Though the four rows of eyelets 604 are evenly spaced in the longitudinal direction, each of the first three rows of eyelets (beginning at the proximal end) 610 of body 402 has a pair of eyelets spaced a first distance from the central axis of the body, while the fourth row has a pair of eyelets spaced closer to one another and closer to the central axis of the body. Nonetheless, the pattern of eyelets 604 in this commissure feature 600 is also symmetrical with respect to the central longitudinal axis of body 602, the row in which the eyelets are spaced closer to one another need not be the fourth row, but may be any row. In addition, the eyelets may be spaced closer to one another in more than one row. Spacing may depend on leaflet thickness and where the free edge transitions so as to not pinch the leaflets too tightly together or abrade the free edge of the leaflet as it moves.

Figure 6C:
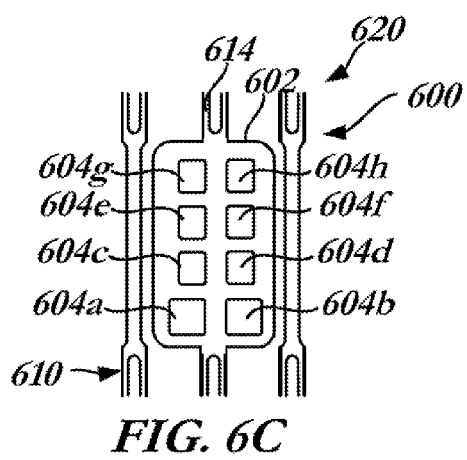

Another embodiment of commissure feature 600 is depicted in FIG. 6C. In this commissure feature, eyelets 604 are not all the same size. Instead, the first row of eyelets (beginning at the proximal end 610 of body 602) includes larger square eyelets 604a and 604b, while the next three rows include smaller, rectangular eyelets 604c-h. While depicted in the first row, the larger square eyelets can be in any row, and in more than one row. All four rows of eyelets may be evenly spaced in the longitudinal direction, and the pattern of eyelets is symmetrical with respect to the central longitudinal axis of body 602.

Figure 6D:
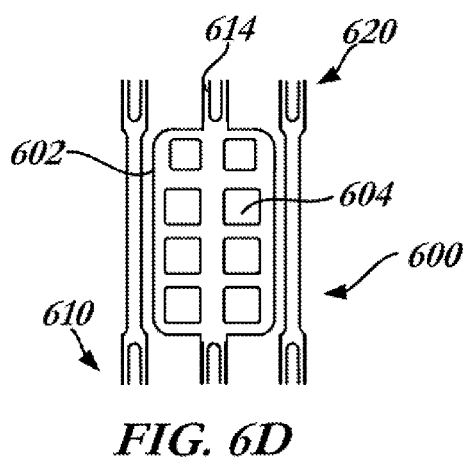

FIG. 6D illustrates another embodiment of commissure feature 600 including four rows of eyelets 604 having the same shape but different sizes. The first three rows of eyelets 604 (beginning at the proximal end 610 of body 602) are all squares of substantially the same size, while the fourth row has square eyelets 604 of a smaller size. The row of eyelets having a different size (smaller or larger) need not be the fourth row, but may be any row. Moreover, the different-sized eyelets need not be limited to one row, but may be disposed in any number of rows. Regardless of the eyelets sizes, the pattern of eyelets 604 in this commissure feature is symmetrical to the central longitudinal axis of body 602.

Figure 6E:
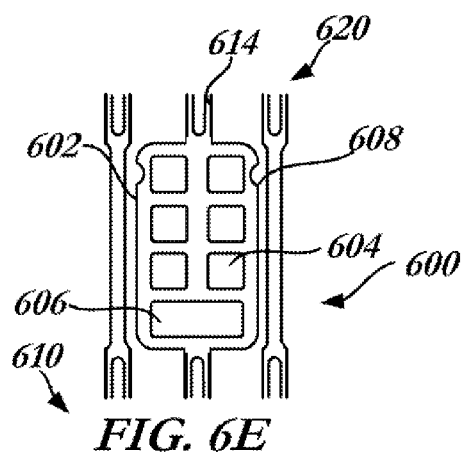

In another embodiment of commissure feature 600, illustrated in FIG. 6E, three rows of substantially the same size square eyelets 604 are disposed toward the distal end 620 of body 602 and a single, elongated eyelet 606 is disposed near the proximal end 610 of the body. This commissure feature further includes a pair of recesses 608 disposed on the side edges of body 602 near the distal end 620.

Figure 6F:
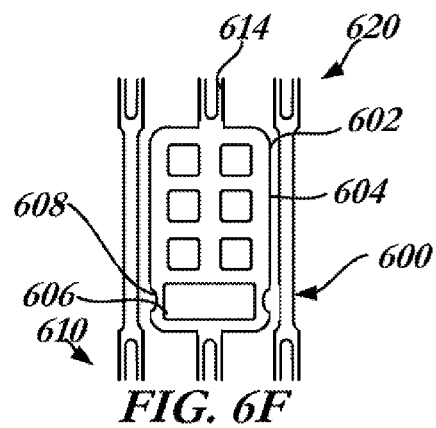

FIG. 6F illustrates an embodiment of commissure feature 600 that is similar to that of FIG. 6E, but with recesses 608 disposed near the proximal end 610 of body 602 (adjacent the single eyelet 608). The eyelets 604 in this commissure feature may be larger or smaller than those in the commissure feature of FIG. 6E.

Figure 6G:
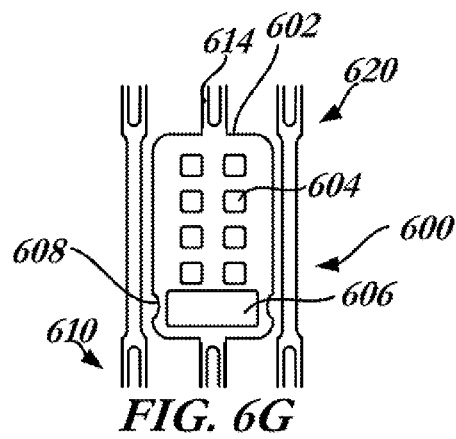

FIG. 6G illustrates an embodiment in which commissure feature 600 includes four rows of eyelets 604 and an additional elongated eyelet 608. It will be understood from this embodiment that the number of rows of eyelets 608 may be varied as desired. Body 602 further includes recesses 608 near its proximal end 610.

Figure 6H:
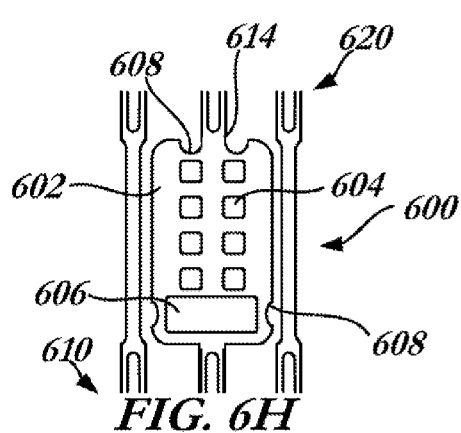

The commissure feature 600 of FIG. 6H is substantially the same as that of FIG. 6G, but includes additional recesses 608 on the distal end 620 of body 602 adjacent either side of the strut 614.

Figure 6I:
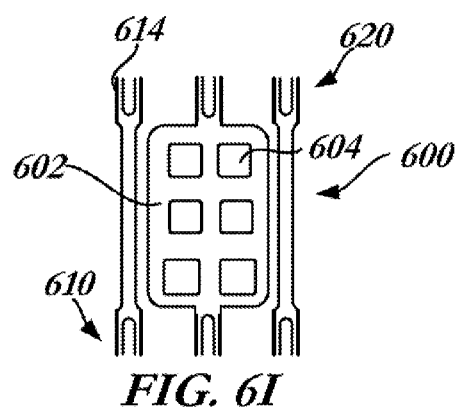

A commissure feature 600 with a slightly shorter body 602 is illustrated in FIG. 6I. This commissure feature includes three rows of eyelets 604 which are substantially evenly spaced on body 602. The eyelets 604 in the first row (beginning at the proximal end 610 of body 602) are slightly larger than those in the second and third rows. They also may be slightly smaller than the eyelets in the other rows. The row of eyelets having a different size (smaller or larger) need not be the first row, but may be any row. Further, the different sized eyelets need not be limited to one row, but may be disposed in any number of rows. Although commissure feature 600 is depicted in FIG. 6I as slightly shorter but about the same width as the commissure features depicted in FIGS. 6A-6H, the commissure feature of FIG. 6I may have a body 602 that is slightly wider than those of the other figures.

Figure 6J:
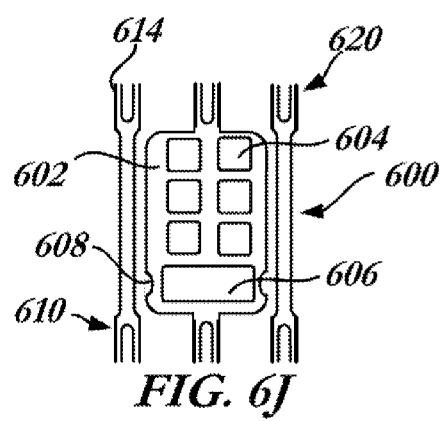

FIG. 6J illustrates yet a further embodiment of commissure feature 600 having three rows of eyelets 604 of substantially the same size and shape disposed on the shorter, body 602. Additionally, this commissure feature includes a single, elongated eyelet 606 disposed at the proximal end 610 of body 602, and a pair of recesses 608 disposed on the side edges of the body near its proximal end.

FIG. 6K illustrates a commissure feature 600 having three dome-shaped bodies 602 connected in series via struts 614. In this example, each dome-shaped body 602 has a pair of eyelets 604. The two eyelets 604 may be the same size or different sizes as illustrated. As seen in FIG. 6K, commissure feature 600 includes three bodies 602, although it will be understood that commissure feature 600 may include two, three, four, five, six or more bodies 602.

FIG. 6L illustrates a commissure feature 600 having three dome-shaped bodies 602 connected in series via struts 614 similar to that of FIG. 6K. In this example, however, two of the bodies 602 are connected via suspension struts 624. Suspension struts 624 may provide greater flexibility for commissure feature 600 during valve loading into a delivery device, in the process of delivery, and in operation of the heart valve. As seen in FIG. 6L, in one example, suspension struts 624 are formed as a pair of struts that diverge at a first body and begin to converge halfway before meeting at a second body 602. Suspension struts 624 may be formed in the shape of a diamond as shown in FIG. 6L. Alternatively, instead of diamond-shaped struts, struts 624 may form a serpentine spring, flat coil. Bodies 602 may also be disjointed or connected by suture, fabric and/or a polymer. In at least some examples, struts 624 may include radiopaque markers, interlocks for valve-in-valve configurations, or delivery system interlock sites. Additionally, though shown between bodies 602, struts 624 may be disposed above and/or below each of the bodies.

As seen in FIG. 6M, the commissure feature need not include three identical dome-shaped bodies, but may include oval bodies 602 having single eyelets. Oval bodies 602 may be disposed in series at the end of the commissure feature 600 or may alternate with other multiple-eyelet bodies in a column. It will be understood that suspension struts 624 may connect any or all of the bodies described herein.

FIG. 6N illustrates a commissure feature 600 having a dome-shaped body 602 connected to a second body 602 having a square configuration and four eyelets 604. Thus, in this configuration, one body includes a single column of eyelets, while a second body includes multiple columns of eyelets 604. As seen in FIGS. 6N and 6O, different-shaped bodies may be connected by single struts 614 or suspension struts 624.

Two square-shaped bodies 602 may be connected to form a commissure feature 600 as seen in FIG. 6P. As seen in this configuration, each body 602 includes four eyelets 604 arranged in two rows and two columns. Suspension struts 624 connect the two square-shaped bodies.

FIGS. 6Q and 6R illustrate two additional examples in which the commissure features include square-shaped bodies connected to rectangular bodies. In FIG. 6Q, a square-shaped body is connected to a rectangular body 602 having two columns of three eyelets 604. These two bodies 602 are connected via suspension struts 624. In the examples shown in FIG. 6R, the square-shaped body 602 is connected to a rectangular body 602 having two rows, each row having three eyelets 604.

FIG. 6S illustrates a commissure feature having a dome-shaped body 602 connected to a rectangular body having two rows of eyelets, each row having three eyelets 604. It will be understood that the present invention contemplates various combinations of oval, dome-shaped, square. Moreover, the eyelets may also be circular, rectangular, trapezoidal as well as any other suitable shape.

Although the commissure features have been described herein as having three or four row of eyelets, any number of rows and/or columns of eyelets may be used, each row and/or column having any number of eyelets. Preferably, the commissure features have at least two rows of eyelets, more preferably at least three rows of eyelets, with at least two eyelets in each row (in other words, at least two columns of eyelets). Moreover, the shapes and sizes of the eyelets in one or more rows may be the same as or different from the shapes and sizes of the eyelets in the other rows. Preferably, however, the shapes and sizes of the eyelets within each row are substantially the same so that the commissure feature has substantial symmetry with respect to the central longitudinal axis of body 602.

Figure 7A:
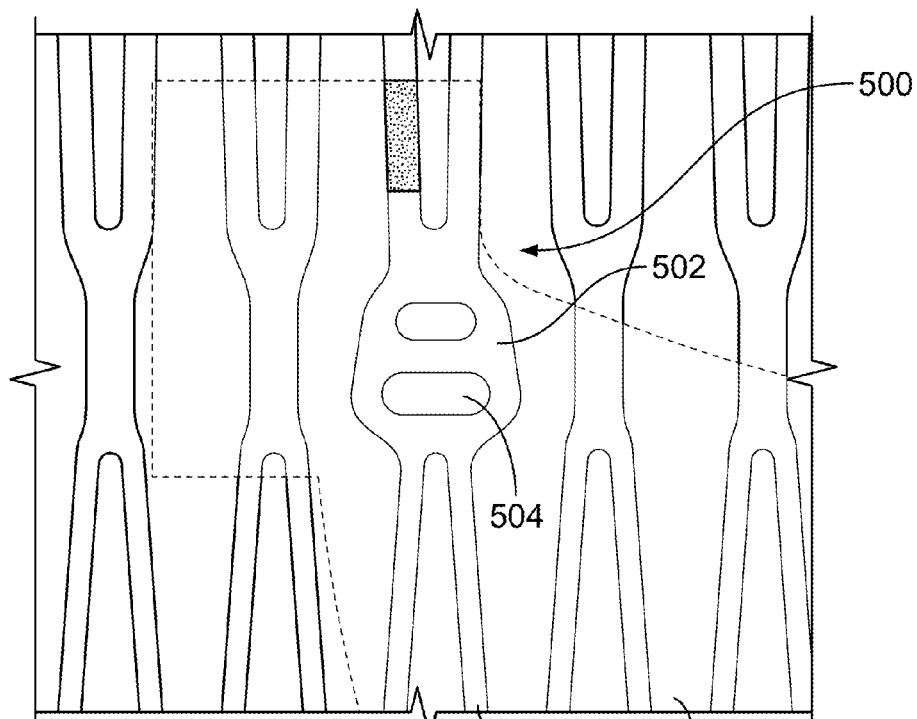
FIG. 7A is an enlarged, schematic side view of the commissure feature of FIG. 5A being attached to a leaflet.
Figure 7B:
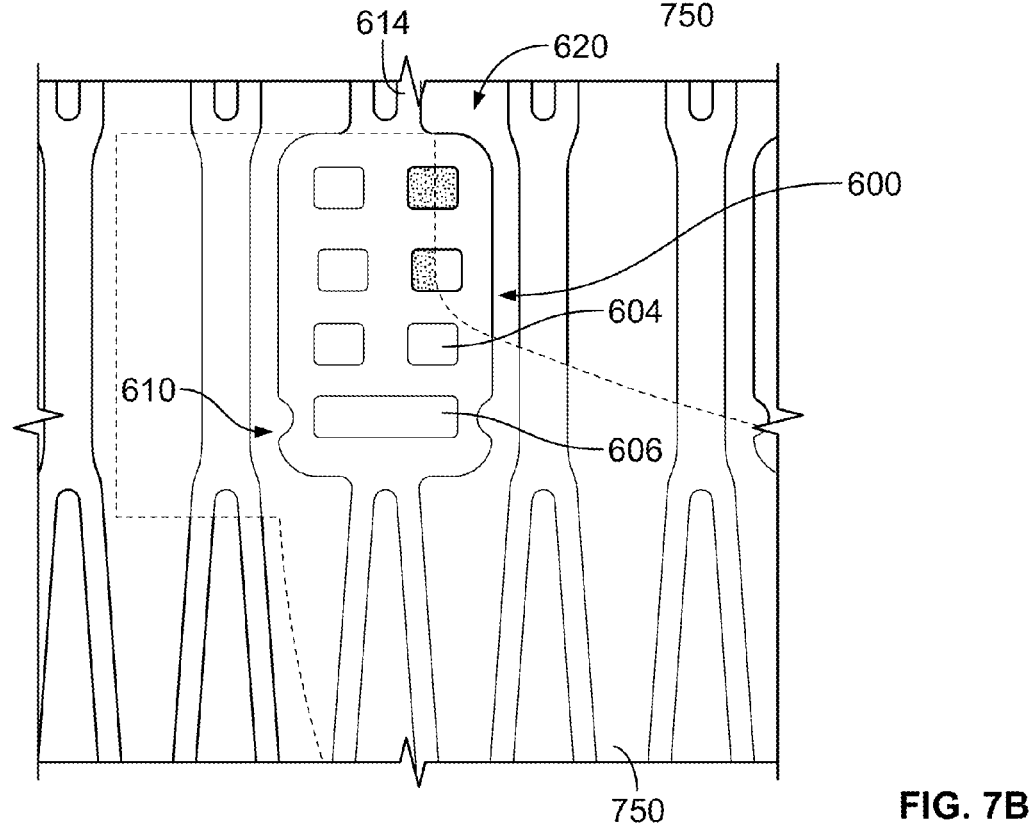
FIG. 7B is an enlarged, schematic side view of the commissure feature of FIG. 6F being attached to a leaflet.

FIG. 7A illustrates the previous version commissure feature 500, while FIG. 7B illustrates one of the commissure features 600 according to the present invention. Commissure feature 600 is similar to that described above with reference to FIG. 6F and includes an elongated eyelet 606, and three rows of square eyelets 604 having substantially the same size, each row having two eyelets. Commissure feature 600 further includes a pair of recesses 608 near the proximal end of body 602 for severally attaching a suture to the body. A silhouette of the end of a leaflet 750 is superimposed over the commissure feature in each figure. As seen by comparing FIGS. 7A and 7B, commissure feature 600 has a larger area and more eyelets than commissure feature 500. As a result, leaflet 750 maybe supported by a larger area with commissure feature 600 then with commissure feature 500. Thus, the load exerted on leaflets 750 may be distributed more uniformly over a larger area with commissure feature 600, resulting in better performance and less likelihood of failure as compared to commissure feature 500. Moreover, as will be discussed in greater detail, suture attachment to commissure feature 500 typically results in a terminating knot in a cell of the stent below the commissure feature 500. Instead, as will be described below, termination of the suture attachment is disposed in the most distal eyelet within the commissure feature. The top portion of leaflet 750 may be aligned above, below or in-line with the top of the commissure attachment.

Figure 7C:
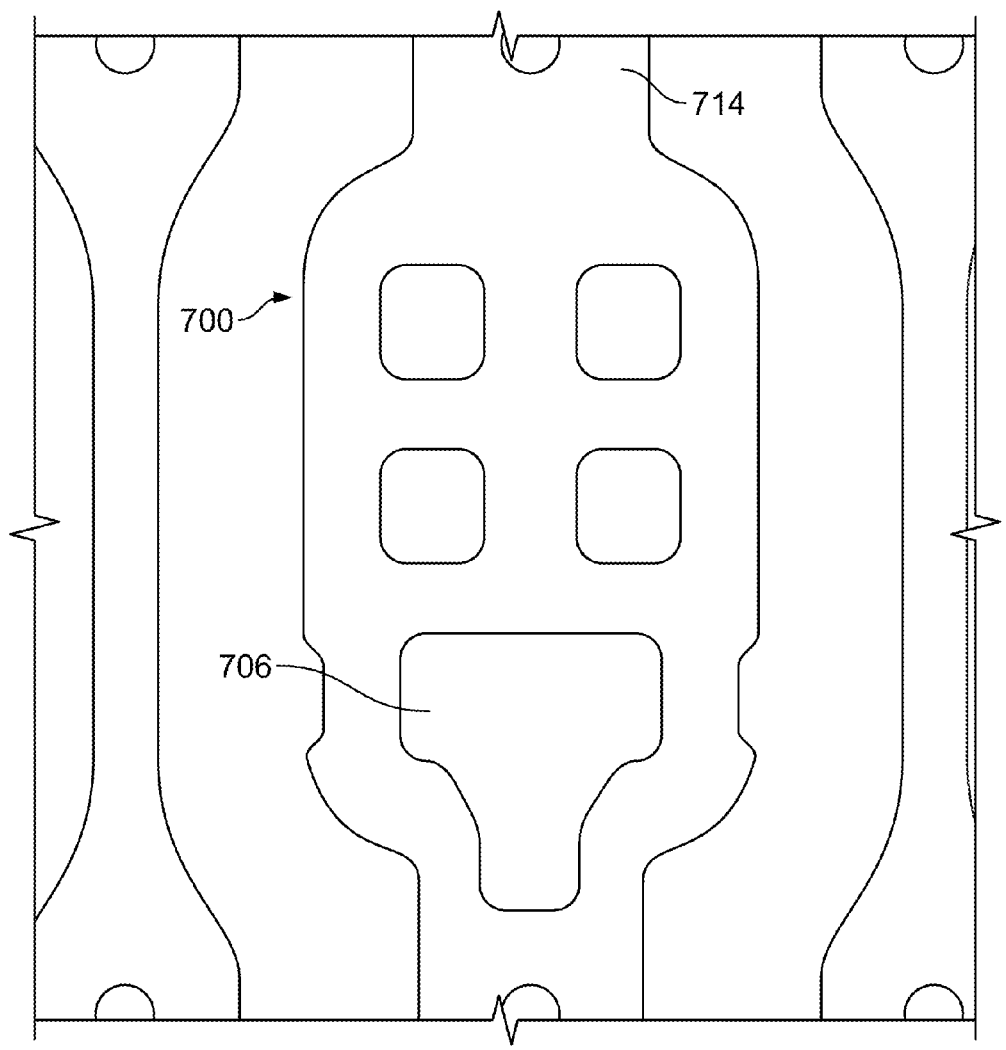
FIG. 7C is an enlarged, schematic side view of another example of a commissure feature according to the present invention.

FIG. 7C illustrates another example of a commissure feature according to the present invention. Commissure feature 700 of FIG. 7C combines desirable features of both commissure features 500 and 600 described above. Specifically, commissure feature 700 is both shorter and narrower to allow for more flexibility when tracking over a curve. Moreover, when collapsed, commissure feature 700 is less likely to interfere with adjacent struts because it can nest within thin support struts between the aorta and annulus sections without interference. The suture attachment is allowed to terminate in the bottom T-shaped eyelet 706 of commissure feature 700. Additionally, the leaflet belly suture itself may terminate within the commissure feature so as to protect it during crimping, loading, resheathing, and distortion after implant.

Figure 8A:
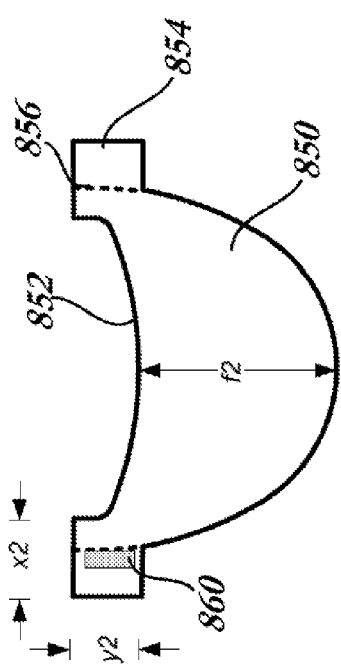
FIG. 8A is an enlarged, schematic side view a conventional valve leaflet.
Figure 8B:
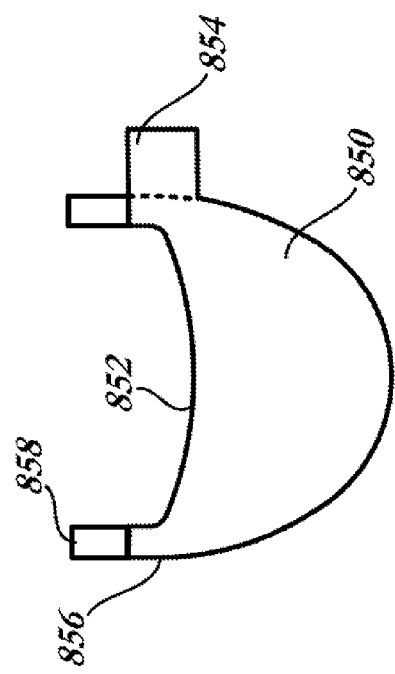
FIG. 8B is an enlarged, schematic side view of a first embodiment of a valve leaflet according the present invention.
Figure 8C:
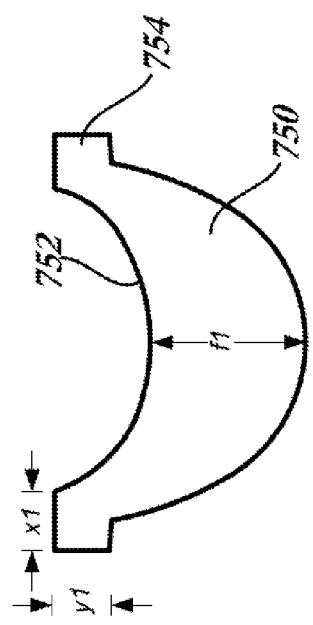
FIG. 8C is an enlarged, schematic side view of a second embodiment of a valve leaflet according to the present invention.

In addition to the improved commissure feature, the leaflets may be constructed to yield improved performance. For example, the size, shape and curvature of the leaflets may be chosen to correspond to the commissure feature to which the leaflets will be attached. FIGS. 8A-C illustrates several embodiments of leaflets exhibiting these design considerations.

FIG. 8A illustrates a previous version of a leaflet 750 having a free edge 752 for coapting with other leaflets and a tab 754 at each end of the free edge for attaching the leaflet to a commissure feature. In some examples, two leaflets may be attached to each other and to a commissure feature.

FIG. 8B illustrates a leaflet 850 according to the present invention. Leaflet 850 has a free edge 852 for coapting with other leaflets and a tab 854 at each end of the free edge for attaching the leaflet to a commissure feature. As seen by comparing the leaflets in FIGS. 8A and 8B, the dimensions and shapes of a leaflet may be modified to improve performance. Specifically, the tab 754 of leaflet 750 is formed with height y1 and width x1. While this height and width may be sufficient to fully cover the previous version commissure feature 500, they may be too small to fully cover the longer commissure features 600 of the present invention. In contrast, the tab 854 of leaflet 850 may have an increased height of y2, enabling the tab to fully cover, and even extend beyond the height of, commissure feature 600. Tab 854 may also have a greater width x2 than tab 754. This greater width provides tab 854 with a greater area to fold about fold line 856 and attach to a commissure feature 600, thereby providing leaflet 850 with greater abrasion resistance. The height of the belly portion of the leaflets may also be modified. As seen in FIG. 8A, leaflet 750 has a belly height of f1 between the bottom of the leaflet and the free edge 752. In contrast, the belly height f2 of leaflet 850 may be greater. Without being bound by any particular theory, it is believed that the greater belly height of leaflet 850 may allow for better leaflet coaptation in elliptical and other distorted configurations.

FIG. 8B further illustrates the use of an additional reinforcement material 860 being used as a stress distributor, reinforced and buffer. A thin layer of reinforcement material 860 may be is sandwiched and/or disposed between the folded layers of tab 854. The tab 854 may be folded over the reinforcement material 860 to provide additional strength and support to the leaflet-commissure attachment area. The reinforcement material 860 may be a fabric, tissue or polymer sheet material and may be attached via sutures, bioglue, weaving and or slots in the reinforcement material.

Figure 8D:
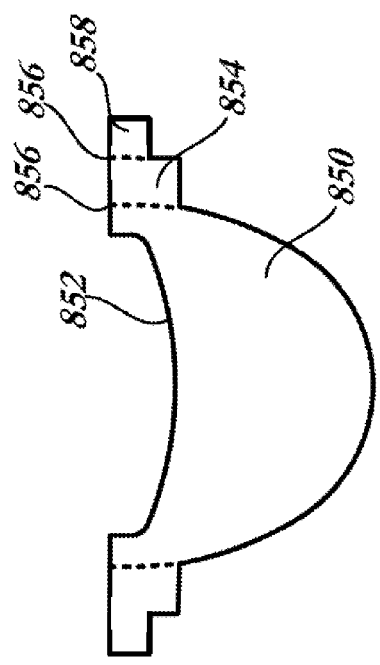
FIG. 8D is an enlarged, schematic side view of a third embodiment of a valve leaflet according to the present invention.

As seen in FIGS. 8C and 8D, additional material may be attached to tabs 854 in the tabs may be formed with additional structures. For example, in FIG. 8C, each tab 854 includes an additional flap 858 and an additional fold line 856. Flaps 858 may be formed unitarily with tabs 854 or separately and then attached to the tabs. Flaps 858 may be formed from the same material as tabs 854 or join a different material. The additional flap 858 may be disposed on the top of tab 854, as shown in FIG. 8D. In addition, leaflet 850 may have a single elongated tab 854 on only one side of the leaflet, the elongated tab 854 being wide enough to wrap over an end or tab of the next adjacent leaflet before attaching to a commissure feature.

Figure 9A:
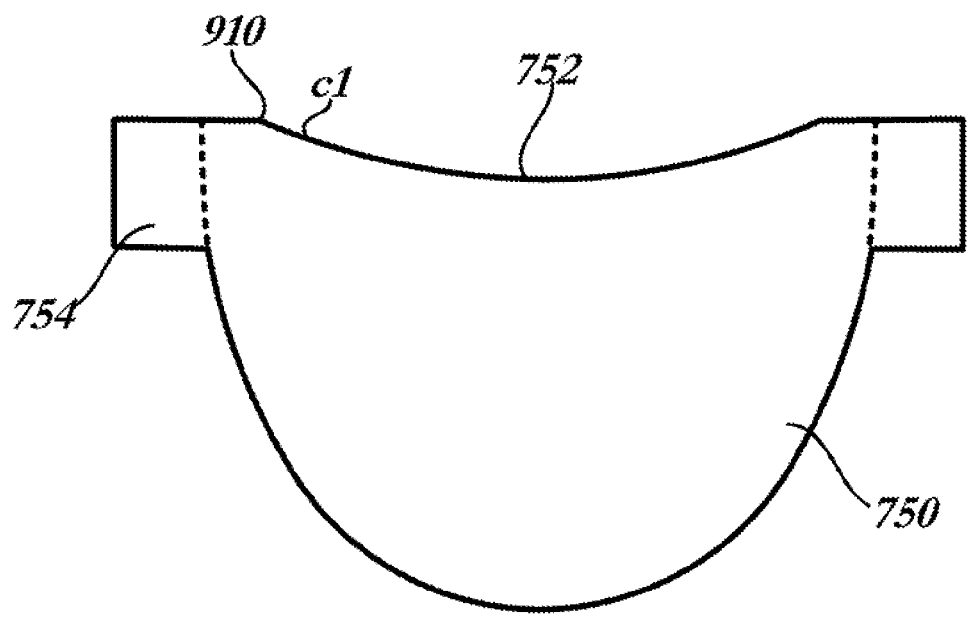
FIGS. 9A-B are enlarged, schematic side views of a conventional leaflet and a leaflet according to the present invention, showing the tab-free edge attachment.
Figure 9B:
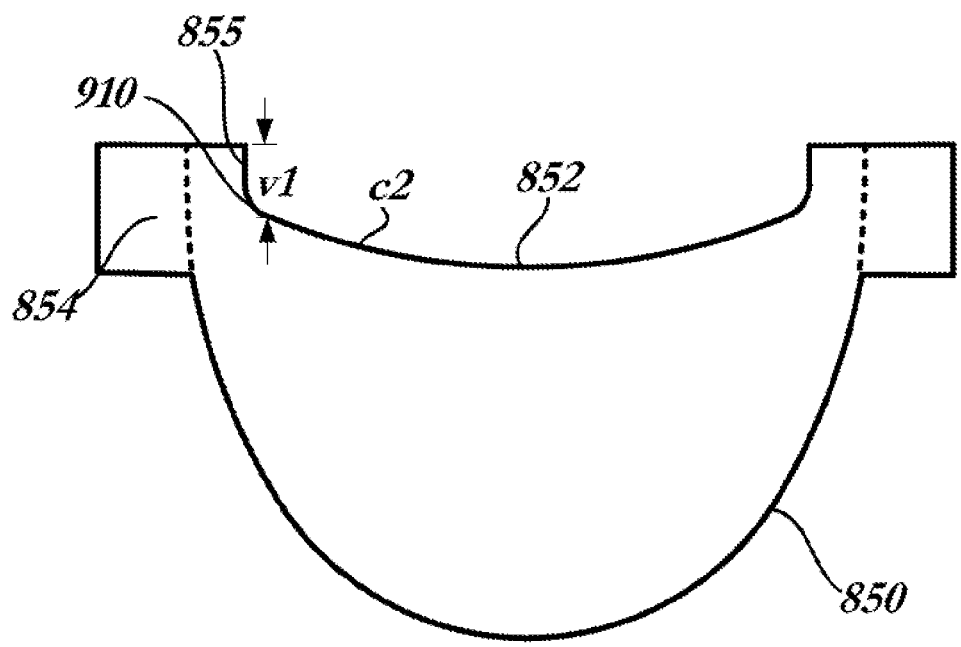

The size and shape of the free edge of the valve leaflets may also be modified to further improve performance. As seen in FIG. 9A, free edge 752 of leaflet 750 has a curved portion c1 which attaches to tab 754 at junction 910. When attached to a commissure feature, especially a larger commissure feature 600, such a configuration may limit the performance and movement of free edge 752. A leaflet 850 according to the present invention may be formed as illustrated in FIG. 9B. Leaflet 850 may include a free edge 852 having a curved portion c2 coupled to tab 854. Tab 854 may include a substantially vertical edge 855 having a height v1. Curved portion c2 may attach to tab 854 at junction 910 adjacent vertical edge 855. Providing a vertical edge 855 on tab 854 may facilitate suturing of the tab to the commissure feature without interfering with the function of the free edge 852 of the leaflet.

Figure 10B:
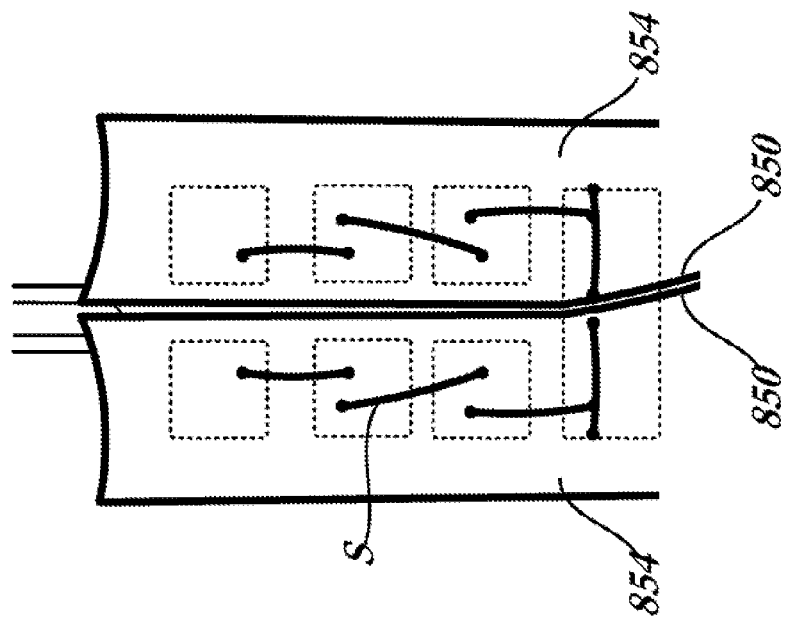
FIGS. 10A-B are enlarged, schematic side views showing a suture pattern attaching leaflets to a commissure feature as shown from the ablumenal side and the lumenal side of the valve, respectively.
Figure 10A:
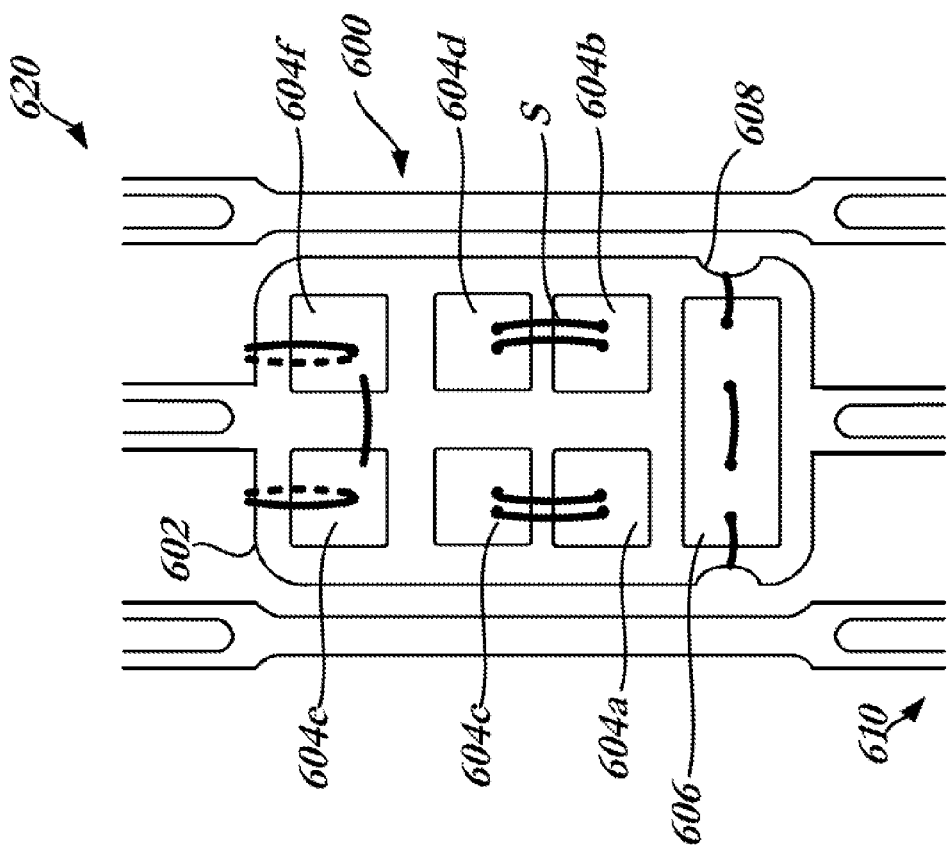

In addition to modifying the commissure feature and the leaflet configuration, the suture pattern attaching the leaflets to the commissure features may also be modified to improve performance. One example of a modified suture pattern according to the present invention is illustrated in FIGS. 10A and 10B. FIG. 10A illustrates the leaflet-commissure feature attachment as seen from the ablumenal side of a valve assembly, while FIG. 10B illustrates the same attachment as seen from the lumenal side of the valve assembly.

As seen in FIG. 10A, a commissure feature 600 includes a body 602 having a proximal end 610 and a distal end 620 similar to the examples described in FIGS. 6A-J. Commissure feature 600 may include a plurality of eyelets 604 disposed toward the distal end 620 of body 602 and a single, elongated eyelet 606 disposed near the proximal end 610 of the body. Commissure feature 600 may also include a pair of recesses 608 disposed on the side edges of body 602 near the proximal end 610 thereof. The plurality of eyelets may include six substantially square eyelets 604 arranged in three rows with two eyelets in each row. Eyelets 604a and 604b are disposed in the first row of eyelets, beginning at the proximal end 610 of body 602. Eyelets 604c and 604d are arranged in the middle row of eyelets, and eyelets 604e and 604f are arranged in the most distal row of eyelets.

As seen in FIG. 10B, the tabs 854 of two different leaflets 850 are attached to commissure feature 600 using a suture or multiple sutures. The following describes the use of, a single suture S to attach leaflets 850 to commissure feature 600. It will be understood, however, that multiple sutures may be used for this purpose. For example, one suture may attach a first leaflet 850 to commissure feature 600, while a second, separate suture attaches the second leaflet 850 to the commissure feature.

The use of a single suture to attach two leaflets 850 to a commissure feature 600 will be described with reference to FIG. 10C, which shows an enlarged view of the leaflet-commissure assembly from the ablumenal side of the valve assembly and depicts the suture pattern through several positions p1-16 on the assembly. It will be appreciated that FIG. 10B shows the corresponding suture pattern from the lumenal side of the valve assembly and that the suture pattern may be understood from this view as well.

The suture pattern may begin at any point at or near commissure feature 600 and terminate at any other point. In at least some examples, the suture pattern begins and terminates at the same position. For the sake of illustration, the suture pattern will be described as beginning at point P1, within eyelet 604b. As used herein, with reference to FIG. 10C and other figures showing the ablumenal side of the valve assembly, the term "out" indicates passing the sutures S from the lumenal side of the valve through the leaflet tab 854 and past the stent structure to the ablumenal side of the valve while the term "in" indicates passing the suture from the ablumenal side of the valve past the stent structure and through the leaflet tab 854 to the lumenal side of the valve.

The suture pattern S may begin by passing suture S out through eyelet 604b at point p1. Suture S may then be advanced in through point p2 in eyelet 604d, back out through point p3 in eyelet 604b, and finally in through point p4 in eyelet 604d, essentially forming two loops of suture S around rib 651. Suture S may then be directed up toward eyelet 604f and passed out through point p5 in eyelet 604f adjacent central spine 655, and then in through point p6 in eyelet 604e adjacent the opposite side of the central spine subsequently, suture S may be passed out through point p7 in eyelet 604c in through point p8 in eyelet 604a, back out through point p9 in eyelet 604c, and back in through point p10 in eyelet 604a, essentially forming two loops of sutures around rib 657. Suture S may then be directed down toward elongated eyelet 606 and passed out through point p11 in eyelet 606, over the side edge of body 602 at point p12 positioned within recess 608, back out through point p13 in eyelet 606, in through point p14 in the same eyelet, around the side edge of body 602 at point p15 within the second recess 608, and in through point p16 in eyelet 606. The tail (not shown) of suture S at point p16 may then be knotted, tied or otherwise joined to the tail (not shown) of the suture at point p1 to complete the attachment of commissure feature 600.

Figure 10C:
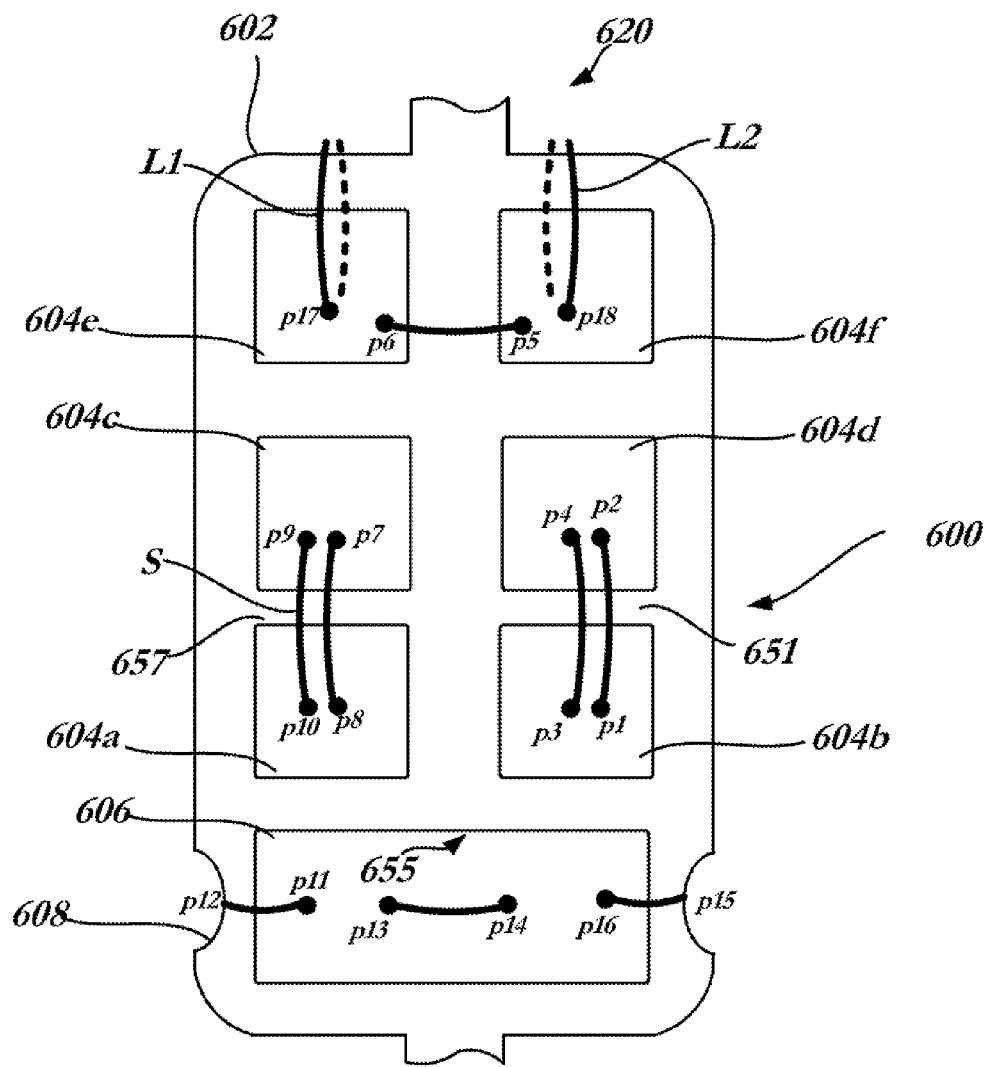
FIG. 10C is an enlarged, schematic view of FIG. 10A showing the attachment points of the suture pattern in more detail.

As seen in FIG. 10C, two optional loops L1 and L2 may be used to tie the leaflets 850 to the commissure feature 600 at the distal end 620 of body 602. Loops L1 and L2 may be formed from one or more lengths of suture separate from suture S. Loop L1 may begin at point p17 in eyelet 604e, and loop over the top of body 602, with the ends of the loop tied together. Loop L2 may form a similar attachment at point p18 in eyelet 604f. As described above with particular reference to FIG. 6H, body 602 may have recesses formed on the distal end 620 of body 602 to aid in securing the loop sutures.

Another example of a suture pattern according to the present invention is illustrated in FIGS. 11A and 11B. FIG. 11A illustrates the leaflet-commissure feature attachment as seen from the ablumenal side of a valve assembly, while FIG. 11B illustrates the same attachment as seen from the lumenal side of the valve assembly.

As seen in FIG. 11A, a commissure feature 600 has a body 602 with a proximal end 610 and a distal end 620 similar to the examples described in FIGS. 6A-J. Commissure feature 600 may include a single, elongated eyelet 606 disposed near the proximal end 610 of body 602 and six substantially square eyelets 604 disposed toward the distal and 620 of the body, the eyelets being arranged in three rows of two eyelets each. Eyelets 604a and 604b are disposed in the first row of eyelets, beginning the proximal end 610 of body 602. Eyelets 604c and 604d are arranged in the middle row of eyelets, and eyelets 604e and 604f are arranged in the most distal row of eyelets. A pair of recesses 608 may be provided in the side edges of body 602 near the proximal end 610 thereof.

As seen in FIG. 11B, the tabs 854 of two different leaflets 850 are attached to commissure feature 600 using a sutures. The suture pattern depicted in FIG. 11A is similar to the pattern described above with reference to FIGS. 10A-C. In addition to the horizontal stitches (as seen in FIG. 11A) within and around elongated eyelet 606 and the vertical stitches (as seen in FIG. 11A) connecting eyelet 604a to eyelet 604c and eyelet 604d to eyelet 604b, the suture pattern incorporates the two most distal eyelets 604e and 604f using an "X" pattern. More particularly, suture S may pass out through eyelet 604f at point p1, travel diagonally over the central spine 655 of body 602 and in through point p2 in eyelet 604e, travel horizontally (as seen in FIG. 11A) under the central spine and back out through point p3 in eyelet 604f, and then travel diagonally over the central spine again (in the opposite orientation) and in through point p4 in eyelet 604e, creating an "X" pattern on the ablumenal surface of the valve assembly. It will be understood that this portion of the pattern may be incorporated as part of a single suture pattern coupled to the suture pattern in the other eyelets 604a-d and/or in the elongated eyelet 606, or may be formed as a separate suture pattern and tied together.

Another example a suture pattern according to the present invention is illustrated in FIGS. 12A and 12B. FIG. 12A illustrates the leaflet-commissure feature attachment as seen from the ablumenal side of a valve assembly, while FIG. 12B illustrates the same attachment as seen from the lumenal side of the valve assembly.

The pattern of suture S illustrated in FIGS. 12A and 12B is similar to that described above with reference to FIGS. 11A and 11B, except that the distal "X" pattern is disposed on the lumenal side of the valve assembly as opposed to on the ablumenal side of the assembly. When viewed from the ablumenal side of the assembly the suture pattern merely reveals a horizontal stitch between eyelets 604e and 604f.

A suture pattern according to the present invention disposed on a commissure feature 600 having only six eyelets is illustrated in FIGS. 13A and 13B. FIG. 13A illustrates the leaflet-commissure feature attachment as seen from the ablumenal side of a valve assembly, while FIG. 13B illustrates the same attachment as seen from the lumenal side of the valve assembly.

The suture pattern, shown in FIGS. 13A and 13B is similar to that described above with references to FIGS. 11A and 11B, without the proximal portion of the pattern incorporating elongated eyelet 606. It will be understood that the patterns described herein are merely exemplary and that combinations of these patterns may be made as desired depending on the particular structure of the commissure feature being used. Moreover, in addition to the overall suture pattern, the order of the pattern may also be modified. For example, the commissure attachment feature may be assembled clockwise or counter-clockwise, front to back, back to front, left to right, right to left, or eyelets may be skipped and then later attached. This allows for different varying levels of security, stress concentrations, abrasion points as well as symmetrical and non-symmetrical attachments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
   a collapsible and expandable stent having an inflow end and an outflow end, the stent including a plurality of commissure attachment features and a plurality of struts defining a plurality of cells, and the stent extending in a length direction from the inflow end to the outflow end; and
   a collapsible and expandable valve assembly including a plurality of leaflets connected to the plurality of commissure attachment features;
   each commissure attachment feature including a body having a proximal end, a distal end closer to the outflow end than the proximal end, and a plurality of eyelets including a selected eyelet having a first rectangular section with a first width in a circumferential direction of the stent and a second rectangular section with a second width in the circumferential direction of the stent smaller than the first width, the selected eyelet including a first interior edge coextensive with a first edge of the first rectangular section and a second interior edge coextensive with a second edge of the second rectangular section.

2. The prosthetic heart valve of claim 1, wherein the plurality of eyelets includes additional eyelets arranged in at least two rows extending in the circumferential direction of the stent and at least two columns extending in the length direction.

3. The prosthetic heart valve of claim 2, wherein each of the additional eyelets is rectangular.

4. The prosthetic heart valve of claim 2, wherein each of the additional eyelets is the same size.

5. The prosthetic heart valve of claim 2, wherein the selected eyelet is positioned closer to the proximal end of the body of the commissure attachment feature than the additional eyelets.

6. The prosthetic heart valve of claim 2, wherein each of the additional eyelets has a size no greater than a maximum size, and the selected eyelet is larger than the maximum size.

7. The prosthetic heart valve of claim 2, wherein the selected eyelet and the additional eyelets are all symmetrically disposed about a center longitudinal axis extending in the length direction from the proximal end of the body to the distal end of the body.

8. The prosthetic heart valve of claim 1, wherein the body of each commissure attachment feature has a peripheral edge and at least one recess formed in the peripheral edge.

9. The prosthetic heart valve of claim 8, wherein the at least one recess is aligned in the circumferential direction of the stent with the selected eyelet.

10. The prosthetic heart valve of claim 9, wherein the at least one recess of the peripheral edge is aligned in the circumferential direction of the stent with the first rectangular section of the selected eyelet.

11. The prosthetic heart valve of claim 8, wherein two recesses are formed in the peripheral edge of each commissure attachment feature, each of the recesses being aligned in the circumferential direction of the stent with the selected eyelet.

12. The prosthetic heart valve of claim 8, wherein the peripheral edge of each commissure attachment feature includes a proximal edge on the proximal end of the body, a distal edge on the distal end of the body, and a pair of side edges between the proximal edge and the distal edge, and the at least one recess is disposed on one of the side edges of the body.

13. The prosthetic heart valve of claim 1, further comprising a suture attaching the valve assembly to the stent, the suture terminating in a knot positioned at least partially within the selected eyelet.

14. The prosthetic heart valve of claim 13, wherein the suture knot is positioned within the second rectangular section of the selected eyelet.

15. The prosthetic heart valve of claim 1, wherein the second rectangular section of the selected eyelet is positioned closer to the proximal end of the body of the commissure attachment feature than the first rectangular section.

16. The prosthetic heart valve of claim 1, wherein the selected eyelet is symmetrically disposed about a center longitudinal axis extending in the length direction from the proximal end of the body to the distal end of the body.

* * * * *